Figure 1:
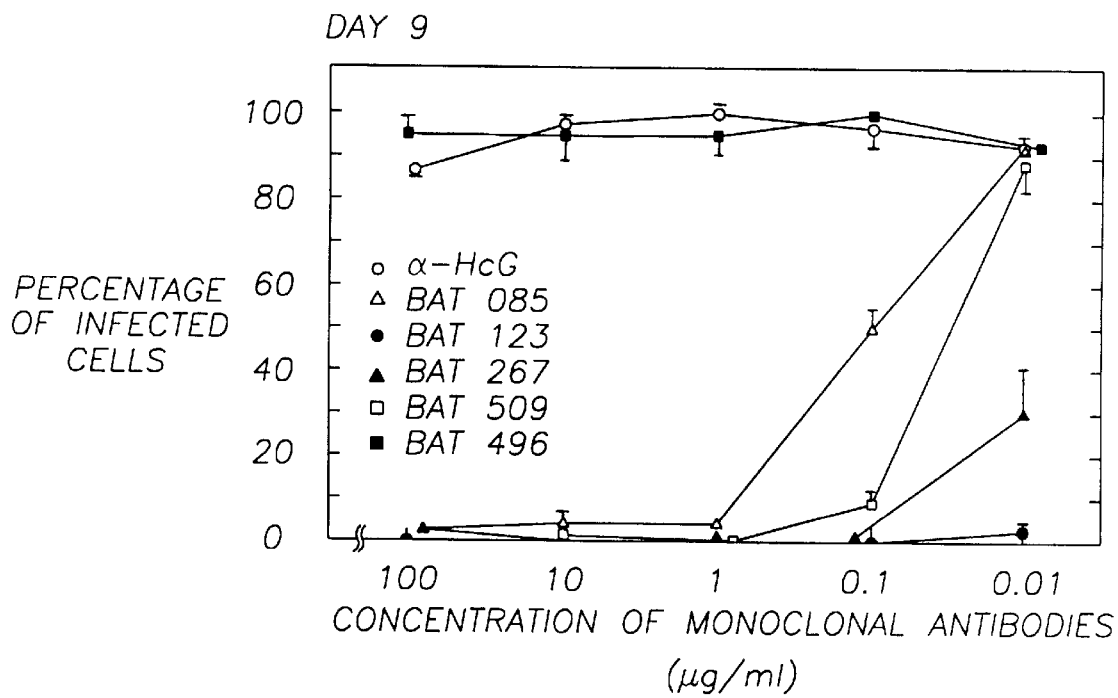

United States Patent [19]
Chang et al.

[11] Patent Number: 5,834,599
[45] Date of Patent: Nov. 10, 1998

[54] IMMUNOCONJUGATES WHICH NEUTRALIZE HIV-1 INFECTION

[75] Inventors: Tse-Wen Chang; Sek C. Fung; Cecily Rou-Yun Sun; Bill Nai-Chau Sun; Nancy T. Chang, all of Houston, Tex.

[73] Assignee: Tanox Biosystems, Inc., Houston, Tex.

[21] Appl. No.: 26,276

[22] Filed: Mar. 4, 1993

Related U.S. Application Data

[63] Continuation-in-part of Ser. No. 895,197, Jun. 5, 1992, abandoned, which is a continuation of Ser. No. 343,540, Apr. 25, 1989, abandoned, which is a continuation-in-part of Ser. No. 137,861, Dec. 24, 1989, abandoned, which is a continuation-in-part of Ser. No. 57,445, May 29, 1987, abandoned.

[51] Int. Cl.$^6$ .................................................. C07K 16/00
[52] U.S. Cl. ................................ 530/388.35; 530/391.7; 530/387.9
[58] Field of Search ........................... 530/391.7, 388.35, 530/387.9

[56] References Cited

U.S. PATENT DOCUMENTS 4,664,911  5/1987  Uhr et al. .

FOREIGN PATENT DOCUMENTS

| | | |
|---|---|---|
| 0125023 | 4/1984 | European Pat. Off. . |
| 0129434 | 6/1984 | European Pat. Off. . |
| 0171496 | 3/1985 | European Pat. Off. . |
| 0199301 | 4/1986 | European Pat. Off. . |
| 0248534 | 5/1987 | European Pat. Off. . |
| 0279688 | 8/1988 | European Pat. Off. . |
| 3727703 | 5/1988 | Germany . |
| 2137631 | 3/1984 | United Kingdom . |
| WO 86/01533 | 9/1985 | WIPO . |
| WO 86/02383 | 4/1986 | WIPO . |
| WO 87/02671 | 5/1987 | WIPO . |
| WO 87/02775 | 5/1987 | WIPO . |
| WO 8809181 | 1/1988 | WIPO . |

OTHER PUBLICATIONS

Fahey et al. Clin. Exp. Immun. 88:1–5 (1992).
Matsushita et al. Aids Research and Human Retrovirus vol. 6, 1990, 193.
Matsushita et al. Journal of Virology 62:2107 1988.
Thorpe. Monoclonal Antibodies '84, pp. 475–506. 1985.
Kennedy et al. Journal of Biological Chemistry. vol. 262 No. 12 25 Apr. 1987, pp. 5769–5774.
French Patent Abstract 2,603,107 Shriver et al. Feb. 26, 1988.
Lambert et al. J. Biol. Chem. 260(22) 12035–41 1985.
Chang et al., PCT Intl. Application, WO 8809181 A2 Dec. 1, 1988.
M. Robert–Guroff, et al., *Nature*, 316: 72–74 (1985).
R.C. Kennedy, et al., *Science*, 231: 1556–1559 (1986).
B.R. Starcich, et al., *Cell*, 45: 637–648 (1986).
M. Alizon, et al., *Cell*, 46: 63–74 (1986).
L.A. Laskey, et al., *Science*, 233: 209–212 (1986).
W.G. Robey, et al., *Proc. Natl. Acad. Sci. USA*, 83: 7023–7027 (1986).
J.D. Lifson et al., *Nature*, 323: 725–728 (1986).
S.D. Putney, et al., *Science*, 234: 1392–1395 (1986).
Weiss et al. "Variable and Conserved Neutralization Antigens of Human Immunodeficiency Virus" Nature 324: 572–75 (1986).
Ho et al. "Human Immunodeficiency Virus Neutralizing Antibodies Recognize Serval Conserved Domains on the Envelope Glycoproteins" J. Virol. 2024–8 (1987).
Naylor et al. "Human Immunodeficiency Virus Contains an Epitope Immunoreactive with Thymosin α1 and the 30–Amino Acid Synthetic p. 17 Group–Specific Antigen Peptide HGP–30" Proc. Nat'l. Acad. Sci. USA 84:2951–55 (1987).
PCT International Search Report (7 pages) Issueb by the EPO.

*Primary Examiner*—Frank C. Eisenschenk
*Attorney, Agent, or Firm*—Eric P. Mirabel

[57] ABSTRACT

Monoclonal antibodies are revealed which bind to the gp 120 protein on the envelope of HIV-1. These antibodies neutralize HIV-1. They inhibit the infection of T cells, and also inhibit syncytium formation. Further, the antibodies are group-specific and neutralize different strains and isolates of HIV-1. These antibodies have a variety of uses, including the treatment and prevention of AIDS and ARC. The antibodies are used in immunotoxins which are specifically toxic to HIV-1 infected T cells.

4 Claims, 6 Drawing Sheets

IMMUNOCONJUGATES WHICH NEUTRALIZE HIV-1 INFECTION

RELATED APPLICATION

This is a continuation-in-part of application Ser. No. 07/895,197, filed on Jun. 5, 1992, now abandoned which is a continuation-in-part of Ser. No. 07/343,540, filed Apr. 25, 1989, now abandoned which is a continuation-in-part of Ser. No. 07/137,861, filed Dec. 24, 1987, now abandoned which is a continuation-in-part of Ser. No. 07/057,445, filed May. 29, 1987, now abandoned.

Field of Invention

The invention relates to monoclonal antibodies which bind to the human immunodeficiency virus-type 1 (HIV-1) and inhibit the infection of T cells.

BACKGROUND OF THE INVENTION

Acquired Immune Deficiency Syndrome, generally known by its acronym AIDS, is probably the most serious health threat confronting society. The disease runs a painful and debilitating course and usually results in the death of its victim. In fact, from diagnosis onward, the average life span of an AIDS victim is less than two years, To date, about 40,000 AIDS cases have been reported in the United States. Approximately two-thirds of individuals have died from the disease.

AIDS is caused by a virus which has at various times been called human T-cell lymphotropic virus type III (HTLV III), or lymphoadenopathy-associated virus (LAV). The virus is currently known as human immunodeficiency virus I (HIV-1). It is estimated by the Center for Disease Control, U.S. Public Health Services, and the National Academy of Sciences that in the United States alone, about 1.5 million people will have been infected by 1991. The results from many long-term epidemiological studies indicate that twenty to sixty percent of the infected group will develop AIDS within the next five to seven years. For example, the Center for Disease Control has estimated that there will about 300,000 AIDS cases by the 1991.

HIV-1 also causes a somewhat less serious immunodeficiency syndrome clinically defined as AIDS related complex (ARC). ARC will often precede the onset of AIDS. There are currently many more ARC cases than there are AIDS cases. As the number of cases continues to increase, ARC will, in and of itself, become an extremely costly and serious health problem.

AIDS results because infection with HIV-1 damages and eventually destroys the victim's immune system. The immune system is reduced to the point where the victim can no longer ward off secondary opportunistic infections. It is often the secondary infections which debilitate the victim and cause death.

In addition to their susceptibility to secondary infections, AIDS victims frequently develop otherwise rare conditions. A large number develop a rare form of skin cancer known as Kaposi's sarcoma. It is believed that this condition also results from the immunodeficiency brought on by the virus.

HIV-1 damages the immune system by infecting and depleting T helper/inducer lymphocytes (hereinafter referred to "T cells"). T cells are essential because they control the production of antibodies by the B cells, the maturation of cytotoxic T lymphocytes (killer T cells), the maturation and activity of macrophages and natural killer cells, and, directly and indirectly, numerous other regulator and effector functions of the immune system.

Infection of a T cell occurs through interaction between an epitope borne by HIV-1 and a receptor site which is located on the T cell surface. This receptor site on the T cell is protein molecule known as the CD4 antigen. The epitope on HIV-1 is borne by the envelope glycoprotein gp 120 (molecular weight 120,000 daltons). The glycoprotein gp 120 is produced when a precursor glycoprotein gp 160, made in the T cell, is cleaved apart into gp 41 (molecular weight 41,000 daltons) and gp 120. Gp 41 bears the epitope which induces the dominant antibody response in most infected individuals, whereas the epitope borne by gp 120 binds to the CD4 antigen and thereby allows the virus to enter the cell.

HIV-1 is a retrovirus. After the virus has entered the cell, a viral enzyme called reverse transcriptase transcribes the viral genomic RNA into DNA in the host cell nucleus. The newly synthesized DNA acts as a template and causes the infected T cell to begin to transcribe the new DNA to make copies of messenger RNA and genomic RNA. The viral genomic RNA's are packed with core proteins, reverse transcriptase, and certain other proteins. They are then enveloped by parts of the cellular membrane and budded off from the cell into the bloodstream as newly synthesized virions. These new virions can enter and infect other T cells.

There are two known mechanisms by which HIV-1 is transmitted to T cells in the body of infected individuals. The first occurs when the free virus binds to the CD4 antigen on the T cells. The second mechanism is through direct, cell-to-cell transmission of the virus.

Direct, cell-to-cell transmission occurs when an infected cell, which expresses the viral gp 120 on its surface, binds with the CD4 antigen of an uninfected cell. As a result the two cells fuse and virions can pass to the uninfected cell.

Direct, cell-to-cell contact and the resulting fusion are a significant source of cellular infection, and may be a major mechanism of T cell destruction in HIV-1 infected individuals. Infected and uninfected cells often fuse in large groups, thereby forming multi-nucleated aggregates known as syncytia. The cell fusion causes the death of cells in the syncytia. See Lifson et al. "Induction of CD4-Dependent Cell Fusion by the HTL-III/LAV Envelope Glycoprotein", Nature 323:725–27 (1986).

The majority of cell death is believed to take place in syncytia. Concentrations of free virus in the bloodstream of infected individuals are typically very low, suggesting that significant infection does not occur as a result of free virus in the bloodstream. Because of the low relative numbers of infected T cells, it also seems unlikely that significant cell infection can occur from discrete fusion of individual infected and uninfected cells. In one study it was found that the proportion of infected T cells in infected individuals is usually only one out of every 10,000 to 100,000 white blood cells. Nevertheless it was reported that the number of CD4 positive cells (i.e., T cells) gradually decreased.

Patients who are infected by HIV-1 typically have very low titers of neutralizing antibodies in their serum, insufficient to neutralize the HIV-1 infection. Thus, monoclonal antibodies which neutralize HIV-1 would be particularly useful for treatment.

Monoclonal antibodies are produced by hybridoma cells. Hybridomas are cells which have all been cloned from a single fused cell. All the clones are identical to the parent. Accordingly, all the hybridomas of the same clone produce identical antibodies which bind to the same epitope.

A method of making monoclonal antibodies was first described by Koehler and Milstein. See Kohler and Milstein,

*Nature* 256:495–97 (1975); Koehler et al., *Eur J. Immunol.*, 6:511–19 (1976). A host animal, usually a mouse, is immunized with an antigen and then sacrificed. Lymphocytes containing B-cells are then removed, usually from the spleen or other lymphoid tissues. The removed lymphocytes are fused with myeloma cells to form hybridomas. The hybridomas which produce antibody against the designated epitopes of the immunizing antigen are cloned and screened. These hybridomas are then used to manufacture the desired monoclonal antibodies.

A monoclonal antibody which inhibits infectivity and syncytium formation would have many advantages over other neutralizing agents. Among the advantages are that large quantities of the monoclonal antibody can be produced, and that hybridomas are immortal due to the fusion with myeloma cells, and thus can be maintained almost endlessly.

Another advantage of monoclonal methodology is that monoclonal antibodies of high specificity and high affinity can be screened and isolated from a large number of antibodies of diverse reactivities and affinities. Antibody of high specificity and high affinity may allow therapeutic use of very small quantities of antibody sufficient to neutralize the virus and to prevent syncytia formation.

The high specificity of monoclonal antibodies is in contrast with that of other neutralizing agents. In one study, antisera were collected from goats which had been immunized with various proteins from the envelope of HIV-1, including gp 120. The antisera effectively blocked infection of HIV-1 only at low dilutions. See S.D. Putney et al., "HTLV-III/ LAV- Neutralizing Antibodies to an E. coli-Produced Fragment of the Virus Envelope", *Science* 234:1392–95 (1986). Similarly, antisera from rabbits and guinea pigs which were immunized with recombinant gp 120 was effective for HIV-1 neutralization only at low dilutions. See L.A. Lasky et al., "Neutralization of the AIDS Retrovirus by Antibodies to a Recombinant Envelope Glycoprotein", *Science* 233:209–212 (1986). The polyclonal antibodies used in these studies were non-specific and therefore had to be used in relatively large quantities.

The above results suggest that entire gp120 and other long recombinant peptides can not induce high titer neutralizating antibodies because the "neutralizating epitopes" may not be immunogenic. Moreover, the antibodies are found to be type-specific and not group-specific, i.e. they react with only the immunizing HIV-1 strain and not with other strains that are genetically significantly different.

In order for a monoclonal antibody to be useful for therapy and prophylaxis against AIDS, it must recognize with high affinity diverse HIV-1 strains and a large number or a significant proportion of field HIV-1 isolates.

In summary, a monoclonal antibody that inhibits infection of susceptible cells by many strains of HIV-1, either by preventing attachment of free visions or by inhibiting direct cell-to-cell transmission of virus through syncytium formation, has great potential therapeutic value. Such an antibody would be useful in treating patients with AIDS or ARC and would be of protective value in preventing AIDS in asymptomatic healthy HIV-1 infected individuals or individuals in high-risk groups for AIDS infection.

SUMMARY OF THE INVENTION

Monoclonal antibodies which bind to the viral envelope glycoprotein gp 120 of HIV-1 have been isolated. The monoclonal antibodies inhibit HIV-1 infection of T cells by free virions, and they also inhibit syncytium formation. Importantly, the monoclonal antibodies are group specific and can neutralize and crossprotect against different strains and different isolates of HIV-1.

The HIV-1-neutralizing antibodies can be used for treatment of AIDS and ARC and for passive immunization against HIV-1 infection. In these procedures, the antibodies can be used as whole antibodies or as antibody fragments or they can be conjugated to cytotoxic or antiviral agents, or to microcarriers which contain such agents in order to target the delivery of these agents to infected cells. The targeted delivery of therapeutic agents can also be achieved with bispecific antibodies derived from the anti-HIV-1 antibodies of this invention which have been provided with a second specificity for the agent to be delivered to the target. Polyclonal or monoclonal antibodies against paratope of the neutralizing antibodies can be used to stimulate a neutralizing immune response against HIV-1.

The monoclonal antibodies of this invention can be used in vivo as antibodies derived wholly from mice or other animals. Alternatively, especially for therapeutic use, the neutralizing monoclonal antibodies can be made in the form of animal/human chimeric antibodies. Preferably, the constant region of the chimeric antibody is human-derived, and the variable region is animal-derived.

The monoclonal antibodies of this invention are produced by continuous, stable antibody-producing cell lines. These cell lines can be produced by hybridoma techniques and by genetic engineering techniques.

This invention also pertains to peptides which correspond to epitopic segments of gp120 recognized by the antibodies of this invention. The peptides can be used in vaccine compositions for generating a crossprotective, neutralizing immune response against HIV-1. They can also be used to detect neutralizing antibodies against HIV-1 in a biological fluid.

BRIEF DESCRIPTION OF THE DRAWINGS

FIG. 1 is a plot showing the relative effectiveness of four of the monoclonal antibodies of the invention in neutralizing HIV-1 infection of H9 cells. The percentage of infected cells was determined nine days after infection.

FIG. 2 is a plot showing the relative effectiveness of four of the monoclonal antibodies of the invention in neutralizing HIV-1 infection of H9 cells. The percentage of infected cells was determined thirteen days after infection.

FIG. 3 is a plot of purification of the immunoconjugate. Immunoconjugate was eluted with a NaCl gradient (—) and absorbance at 280 nm was recorded (—). The immunoconjugate elutes as a single peak at 110 mM NaCl.

FIG. 4 is a flow cytometric analysis plot showing the relative binding activities of the immunoconjugates BAT123-PAP-S and G3.519-PAP-S. BAT123-PAP-S bound greater than 90% of the HTLV-IIIB infected H9 cells at 0.1 ug/ml while G3.519-PAP-S required 10 ug/ml to show the same degree of binding.

FIG. 5 is a plot showing the cytotoxic effects of G3.519-PAP-S when presented to H9 cells infected with HTLV-IIIB, HTLV-IIIMN, or HTLV-IIIRF. The immunoconjugate killed H9 cells infected with HTLV-IIIMN more effectively than it killed H9 cells infected with HTLV-IIIB and HTLV-IIIRF.

FIG. 6 is a plot showing the cytotoxic effects of BAT123-PAP-S when presented to H9 cells infected with HTLV-IIIB, HTLV-IIIMN, or HTLV-IIIRF. BAT123-PAP-S was most effective at killing H9 cells infected with HTLV-IIIB, moderately effective at killing H9 cells infected with HTLV- IIIMN, and relatively ineffective at killing H9 cells infected with HTLV-IIIRF.

Figure 7:
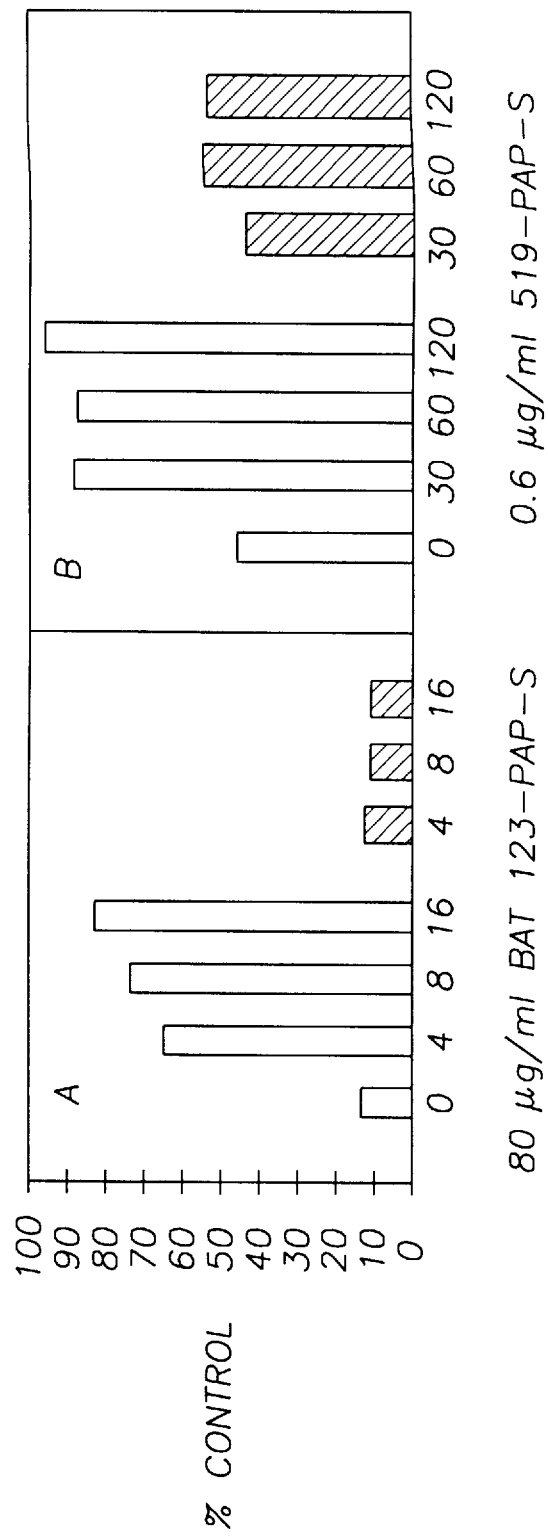

FIG. 7 is a chart showing the specificity of the cytotoxic effects of immunoconjugates. The addition of specific monoclonal antibody to the target cells prior to incubation with the immunoconjugates efficiently and specifically blocks the cytotoxicity of the immunoconjugates in a dose-dependent fashion.

DESCRIPTION OF THE INVENTION

A. Summary of Procedures Used

The monoclonal antibodies of the invention bind to the viral envelope glycoprotein gp 120. In the processing of HIV-1 specific envelope protein in infected T cells, gp 41 is a transmembrane domain and is not exposed. In contrast, gp 120 is an external envelope protein which is extracellular. Thus, in infected T cells the gp 120 protein offers binding epitopes for the monoclonal antibodies of the invention.

The monoclonal antibodies of the invention were found to be effective in inhibiting infectivity and in inhibiting syncytium formation. This indicates that they will likely be very effective for in vivo neutralization, as the majority of cell death is believed to occur in syncytium. Importantly, the antibodies can neutralize different strains and different isolates of HIV-1 (i.e. the antibodies are group specific). The antibodies neutralize infection of cells by different strains and different isolates of the virus. The neutralizing antibodies also inhibit syncytium formation by various strains of HIV-1 which have a substantial degree of heterogeneity in the amino acid sequence of gp 120. These results indicate that antibodies are crossprotective and are able to protect against the various strains of the virus in the population.

The neutralizing antibodies of this invention can have high potency in neutralizing infectivity. For example, the monoclonal antibodies can inhibit, with an $IC_{50}$ of less than 10 ng/ml, the infection of susceptible human T cells lines by HIV-1 $_B$ at 20 times $TCID_{50}$ in a nine day assay.

The general procedure for production of the antibodies is discussed below.

The monoclonal antibodies of the invention were made by conventional techniques which are commonly used in hybridoma production. In brief, mice were immunized with inactivated HIV-1. B cells taken from the spleens of the immunized mice were fused with NS-1 myeloma cells. Polyethylene glycol mixed with dimethyl sulfoxide (DMSO) in calcium magnesium-free phosphate buffered saline (PBS) was used as the fusion reagent. The hybridomas generated from the fusion were then transferred to 96 well microtiter plates and grown.

The hybridomas which produced the monoclonal antibodies that neutralized HIV-1 were isolated by a series of screening procedures. First, an enzyme linked immunosorbent assay (ELISA) was run on the clones in all the wells. In this test, it was determined whether monoclonal antibodies produced by these clones would bind to purified gp 120. Clones from those wells which showed highest reactivities with gp 120 were selected for further screening by an immunofluorescence assay.

The immunofluorescence assay was run to determine which of the ELISA positive monoclonal antibodies would bind specifically to intact, live infected T cells, but not to uninfected T cells. The clones found to be immunofluorescence positive, i.e., those which produced antibody specific to the infected cells, were used in a single-cell cloning.

In single-cell cloning the clones are diluted so that there are only a few cells per given volume. This volume is then added to a well, and the cells are grown. The objective is to attain randomly by binomial distribution in some wells only a single-cell colony per well. This cell colony is monitored visually under a microscope to determine whether it is a monoclonal.

The ELISA-positive clones were also tested in a Western blot analysis. In this procedure lysates of HIV-1 proteins were separated by gel electrophoresis and transferred onto nitrocellulose strips. The supernatants from the ELISA-positive wells are then tested for reactivity with gp 120 protein band on the strips.

At the conclusion of these screening steps, monoclonal antibodies which were specific to the gp 120 and to infected cells had been isolated.

The immunofluorescence-positive hybridomas were then injected into the peritoneum of mice for production of a larger quantity of monoclonal antibodies from the ascites fluid. The antibodies were then purified for assays for neutralization.

A number of modifications of the above immunization, fusion, screening, and method of antibody production are possible. For example, animals other than mice can be used for the immunization. B cells are then obtained from the immunized animal for use in the fusion.

Further, reagents other than those discussed can be used for the chemical fusion. Another alternative is to use electrical fusion rather than chemical fusion to form hybridomas. This technique is well-established. Instead of fusion one can also transform a B-cell to make it immortal using, for example, an Epstein Barr Virus or a tranforming gene. (For a method of transforming a B-cell, See "Continuously Proliferating Human Cell Lines Synthesizing Antibody of Predetermined Specificity," Zurawski, V.R. et al, in *Monoclonal Antibodies,* ed. by Kennett R.H. et al, Plenum Press, N.Y. 1980, pp 19–33.)

With regard to the ELISA, the immunofluorescence assay, and the Western blot analysis, it should be noted that several alternatives of all these steps are possible. One could do a greater or lesser number of screening steps. Or, instead of those which are described, one could substitute other screening procedures, for example, a radio-immunoassay, or an immunohistochemical staining techniques. The important consideration is that the procedure selects for hybridomas which secrete monoclonal antibodies which are specific for gp 120 and which specifically bind to the cell surface of HIV-1 infected T cells.

The single cell cloning procedure can be varied such that various numbers of cells initially are placed into each well. The test for whether there is in fact only one clone present in each well can also be performed by a number of methods.

The method of producing monoclonal antibodies, i.e., injecting hybridomas into mice, can also be varied. It is possible to grow large quantities of monoclonal antibodies in culture using perfusion or hollow-fiber techniques.

After isolation of monoclonal antibodies specific to gp 120 and to intact, live infected cells by the above-described methods, the effectiveness of the antibodies in neutralization of HIV-1 was tested. Monoclonal antibodies from each clone which was immunofluorescence positive were isolated. A comparison was made of the number of cells infected by HIV-1 in the presence or absence of the monoclonal antibodies. Different titers of each antibody were used in order to compare their potency. The neutralization assay was monitored with an immunofluorescence technique.

The second test of neutralization is by syncytium inhibition. In the syncytium inhibition assay infected T cells were added to a well seeded with transfected HeLa cells which had been artificially transfected with CD4 genes and expressed the CD4 antigen on their surface. The CD4 antigen on the cell surface fuses with infected T cells to form multi-nucleated giant cells. It was determined which titers of the immunofluorescence positive antibodies would inhibit giant cell formation.

A great deal of modification of the neutralization assays and their monitoring procedures is possible. It may be desirable to test only one and not the other if, for example, one was concerned only with syncytium formation and not with infection through free virion particles.

The antibodies are tested in these assays for neutralization of different viral strains and isolates.

In conclusion, a variety of ways of preparing and testing the products of the invention are possible and are within the scope of the invention. The advantages and uses for the monoclonal antibodies of the invention will now be discussed.

B. Advantages and Uses

As noted above, one advantage of monoclonal antibodies is their specificity. This specificity is highly pertinent to use of the monoclonal antibodies of the invention in therapy, because it means that lower dosages can be used.

The therapeutic uses for the monoclonal antibodies of the invention include both in vivo immunotherapy and extracorporeal immunotherapy. Direct in vivo treatment with the monoclonal antibodies of the invention involves administering them internally, preferably via intavenous injection. If treatment of infected cells in the brain is needed, it may be possible to couple the monoclonal antibody to an agent, such as certain lipophilic substances, which allows it to pass through the blood-brain barrier. The antibodies of this invention can neutralize different strains and isolates of HIV-1 and thus, they can effectively protect against the different types of virus encountered in the patient population.

In extracorporeal therapy, blood leukocyctes are removed from the patient and treated with neutralizing antibody. The monoclonal antibody is then added to the leukocytes. The leukocytes can also be stimulated with immunopotentiating drugs, for example interleukin-2. The leukocytes are then returned to the patient.

The mouse-derived monoclonal antibodies of the invention can be used for both direct in vivo and extracorporeal immunotherapy. However, it has been observed that when mouse-derived monoclonal antibodies are used in humans as therapeutic agents, the patient produces human anti-mouse antibodies. Thus, it has been said that mouse-derived monoclonal antibodies, at least in some cases, have limited therapeutic value. See V.T. Oi et al., "Chimeric Antibodies," *Bio Techniques* 4(3):214–221 (1986). With established genetic engineering techniques it is possible, however, to create antibodies which have animal-derived and human-derived portions. Chimeric antibodies comprise an antigen-binding (variable) region derived from an animal antibody and a constant region derived from a human antibody. The animal can be a mouse or other rodent such as a rat. If the variable region of the chimeric antibody is mouse-derived while the constant region is human-derived, the chimeric antibody will generally be less immunogenic than a "pure" mouse-derived monoclonal antibody. These chimeric antibodies would likely be more suited for therapeutic use, should it turn out that "pure" mouse-derived antibodies are unsuitable.

Chimeric antibodies can be produced by chimeric DNA constructs which encode the component antibody chains. See V.T. Oi et al., *Bio Techniques* 4(4):214–221 (1986); L.K. Sun et al.,"Chimeric Antibodies with 17–1A-Derived Variable and Human Constant Regions", Hybridoma 5 (1986). Such a DNA construct comprises DNA encoding functionally rearranged genes for the variable region of a light or heavy chain of a HIV-neutralizing antibody linked to DNA encoding the human constant region. Lymphoid cells such as myelomas or hybridomas transfected with the DNA constructs for light and heavy chain can express and assemble the antibody chains.

Another alternative form of monoclonal antibody is a bispecific antibody. Bispecific antibodies carry two different antigen binding portions, both of different specificity. A bispecific monoclonal antibody can have one antigen binding portion derived from the monoclonal antibodies of the invention, and a second antigen binding portion of a specificity for an agent to be targeted to a particular site. For example, the second specificity can be for a surface epitope of a human T cell or of a macrophage, such as the CD4 and CD3 molecules. These bispecific antibodies can be used to target a T cell or macrophage toward an HIV-1 infected cell.

The bispecific antibodies can be single, hybrid antibodies or antibody fragments having a bi-specificity (See M. Brennan, "A Chemical Technique for the Preparation of Bispecific Antibodies from Fab' Fragments of Mouse Monoclonal $IgG_1$", *Biotechniques* 4:424–27 (1986)) or they can be heteroaggregates of two antibodies each having a different specificity.

The potential patient populations for receiving immunotherapy antibody treatments include patients with AIDS or ARC. A variant of immunotherapy is protection through passive immunization. The antibodies of this invention are particularly suitable for passive immunization because they can crossprotect against HIV-1 of different strains in the population. In this procedure, patients who are asymptomatic (not yet showing symptoms of AIDS or ARC), or who are seronegative but in a high risk group, are treated to inhibit infection. The targets include fetuses born in or babies born to HIV-1-carrier mothers and health professionals working with AIDS patients, or blood products, such as dentists and nurses. The agent for treatment, again, can be the monoclonal antibodies of the invention, chimeric mouse/human monoclonal antibodies, or bispecfic monoclonal antibodies.

Most of the research attention in the effort to stop AIDS has focused on the search for a vaccine. In one type of proposed vaccine the immunizing agent is a portion of HIV-1 which itself is non-infective but which nonetheless induces antibody production. Monoclonal antibodies which neutralize HIV-1 can help in the search for such a vaccine. They can be used to help locate, identify, and study the "neutralizing" epitopes on HIV-1 which bind the monoclonal antibodies. These epitopes are likely to be the non-infective but nonetheless immunogenic portion of the molecule. Study of these epitopes allows synthesis of a non-pathogenic immunogen with a structure which is the same or immunologically equivalent to the epitope. For example, the immunogen can be a peptide which comprises an amino acid sequence that is the same or similar to the epitope bound by an anti-HIV-1 antibody which neutralizes HIV-1.

It has now been discovered that two of the neutralizing antibodies of this invention recognize epitopes located in a region of gp 120 having the following amino acid sequence:

RPNNNTRKRIRIQRGPGRAFVTIGK

This segment represents a 25 amino acid residue long segment of gp 120 (residue #294 to residue #318). One antibody (BAT267) reacts with a peptide having the sequence RPNNNTRKRIRIQRG (peptide a) and the other antibody (BAT123) reacts with a peptide having the sequence RIQRGPGRAFVTIGK (peptide b). There are regions corresponding to this segment (IIIB) in other strains of HIV.

These two 15 amino acid residue long peptides represent two adjacent, overlapping segments of gp120of HIV-1B: peptide "a" represents the segment of residue #294 to residue #308 and peptide "b" of residue #304 to #318. BAT267 reacts with peptide "a" and not peptide "b", which shares five amino acids RIQRG, or another 15 amino acid long peptide, which represents a segment of gp120 (residues #284 to #298) adjacent to peptide "a" and shares five amino acids RPNNN. These results suggest that BAT267 recognizes an epitope either borne entirely by all or a part of the middle five amino acid residues TRKRI or formed by all or a part of these five amino acids with some of the flanking amino acid residues. Based on similar results, BAT123 seems to react with an eptiope either borne entirely by all or a part of PGRAF or formed by the combination of all of a part of PGRAF with some of the flanking amino acid residues.

The BAT085 antibody reacts with a peptide having the amino acid sequence VQKEYAFFYKLDIIP.

The peptidic immunogens of this invention can comprise the above-identified amino acid sequences or immunochemical and immunogenic equivalents thereof. These equivalents include, for example, any of the actual epitope portions of any of these sequences, corresponding peptidic regions from various HIV-1 strains and peptides generated by various changes such as insertions, deletions and substitutions of amino acids.

The peptides of this invention can be coupled together to form larger, multivalent oligopeptides.

The peptides may be prepared by chemical synthesis. Alternatively, they may be prepared by recombinant DNA technology where DNA sequences encoding the peptides are synthesized or isolated from HIV-1 DNA and expressed in an appropriate expression system.

The peptides may also be used individually or in combination to elicit a immune response against HIV-1. For this purpose, the peptides may be formulated in vaccine compositions, generally for administration at concentrations in the range of 1 ug to 20 mg/kg of host. Physiologically acceptable vehicles such as water, saline, or phosphate buffered saline can be used in the formulations. Adjuvants, such as aluminum hydroxide gel, can also be employed. The route of administration can be intramuscular, intraperitoneal, subcutaneous, or intravenous. The compositions can be given one time or multiple times, usually at one to four week intervals.

In preferred embodiments of the vaccine composition, the peptides are coupled to a carrier protein such as a foreign keyhole limpet hemocyanin. This can enhance the immunogenicity of the haptenic peptides.

The peptides may be used in immunoassays to identify neutralizing antibody or to screen for the presence of neutralizing antibody in serum.

Another type of vaccine which monoclonal antibodies that neutralize HIV-1 make possible is one based on an anti-idiotype antibody. Antibodies carry "idiotypes", regions near their antigen-recognition sites that are themselves antigenic and capable stimulating antibody production. Antibodies which are specific to the antigen-combining sites are called parotope-specific anti-idiotype antibodies. These antibodies bear the same confirmation as the antigen which initially stimulated antibody production. See J.L. Marx, "Making Antibodies Without Antigens", *Science* 288:162–65 (1986).

Thus, parotope-specific anti-idiotypic antibody with partially the same structure as HIV-1 can be made by immunizing an animal with the monoclonal antibody to HIV-1. These parotope-specific anti-idiotype antibodies, which carry the same structure as the immunogenic portions of the virus, would likely be suitable for use as a vaccine because they would cause an immune response. Advantageously, because these anti-idiotype antibodies consist of protein and do not carry any viral nucleic acid, they would be of much less concern for pathogenicity. A chimeric mouse/human anti-idiotype antibody wherein the variable region is mouse monoclonal anti-idiotype antibody and the constant region is human immunoglobin, is most preferable.

The monoclonal antibodies of the invention can also be used to aid in the delivery of cytotoxic or antiviral agents, by incorporating them into, for example, microcarriers or liposomes. Exemplary cytotoxic agents include pokeweed antiviral protein from seeds (PAP-S), cytotoxic steroids, gelonin, abrin, ricin and phospholipases. Examples of antiviral agents are interferon, azidothymidine and riboviran. Once again, it should be noted that chimeric mouse/human monoclonal antibodies, or bispecific monoclonal antibodies, are also suited to aid in drug delivery.

In the conventional sense, antibodies, including monoclonal antibodies, are referred to as the mediator of humoral immunity. However, because antibodies which are specific for unique cell surface antigens on target cells can be conjugated with cytolytic or cytotoxic agents, the resulting immunotoxins can in effect mediate cellular immunity. Cytotoxic T lymphocytes, which are the key mediator of antigen-specific cellular immunity, recognize and lyse viral-infected cells. Thus, with proper engineering, the antibodies specific to viral antigenic epitopes expressed on infected cell surface can achieve the major function of cytotoxic T lymphocytes.

Conjugates of antibodies and toxins have been actively explored as therapeutic agents for destroying tumor cells in cancer patients (L.E. Spitler, *Immunotoxin,* ed. A.E. Frankel, Kluwer Academic Publishers, Boston, pp 493–514 (1988)). These immunoconjugates are known to exhibit relatively long half-lives in vivo and their side effects in most patients are clinically tolerable (L.E. Spitler, *Immunotoxin,* ed. A.E. Frankel, Kluwer Academic Publishers, Boston, pp 493–515 (1988)). Therefore, a rational approach for treating AIDS patients and HIV-infected individuals is to target the HIV-infected and producing cells by using conjugates of toxins and monoclonal antibodies specific for surface antigens of HIV. Monoclonal antibodies of this invention can be linked to the cytotoxin PAP-S and the resulting immunoconjugate shown to have specific cytotoxicity against human T cells infected with diverse strains of HIV-1. The immunoconjugates of the invention, either alone or in combination, can be immobilized on inert solid matrices or magnetic beads, either directly or indirectly through a cross-linking agent or a specific binding agent (e.g. protein A or goat anti-mouse IgG). The biological fluid test samples are then incubated with the antibody-coated matrices. HIV-1 virions or gp120 reactive with the immunoconjugates will bind to the matrices. The bound virions or gp120 can then be detected with either monoclonal or polyclonal anti-HIV-1 antibodies, which can then be reacted with enzyme-linked secondary detecting antibodies for quantitation based on color reaction. Alternatively, the captured virions can be detected by other means, e.g. fluorescence, chemiluminescence, or PCR.

The immunoconjugates of the invention can be used to detect and to quantitate the HIV-1-infected cells in patient blood samples by direct or indirect immunofluorescence procedures. A sample procedure for how to conduct such an immunofluorescence assay is described in Example I, part (e) below, using monoclonal antibodies (rather than immunoconjugates).

The details for the procedure by which the monoclonal antibodies and immunoconjugates of the invention were made will now be described.

EXAMPLE I
Preparation of the Hybridomas and Monoclonal Antibodies a) Preparation of Virus In order to maintain a supply of inactivated HIV-1, a virus stock was prepared as follows. The H9 clones of the HT cell line (which is described by M. Robert-Guroff et al. in *Nature* 316:72–74, supra) were maintained in culture. These H9 cells were infected with HIV-1 (HTLV IIIB), which was a gift from Dr. R. Ting, Biotech Research Laboratory, Rockville, Md. Maintaining the infected H9 cells in culture permits the cells to reproduce and to continuously synthesize a supply of HIV-1. The H9 cells were cultured in a growth medium of 20% FBS (heat-inactivated) RPMI 1640, supplemented with 5mM L-glutamine, 5mM HEPES, 50 units/ml penicillin and 50 mg/ml streptomycin.

Purified HIV-1 was obtained by first centrifuging the cell culture at 1000 g for ten minutes to remove the cells and debris. The supernatant was then centrifuged at 90,000 g for one hour. The virus pellet was resuspended in minimal volume of phosphate buffered saline pH 7.4 and loaded onto a centrifuge tube with a preformed sucrose gradient (20%–60%). The sample was then centrifuged at 100,000 g for sixteen hours. The virus was collected at the gradient of 38%. The virus was then aliquoted and frozen at $-80°$ C. after the protein content was measured.

b) Immunization Procedure

Male Balb/c mice were used for the immunization. Each mouse received 100 micrograms of inactivated HIV-1. The inactivation of the virus was performed according to FDA approved protocol, by UV irradiation and addition of a detergent, Nonidet P-40 (0.1%). A volume of suspension containing 100 micrograms of virus per mouse was suspended in 200 microliters phosphate buffered saline (PBS), and emulsified with equal volumes of complete Freund's adjuvant.

Each mouse was immunized subcutaneously with 100 micrograms of the emulsified virus. The mice were injected at sites with high concentrations of lymph nodes, for example, the underside of the intersection of the limbs and the trunk. One month later the mice received subcutaneous booster injections at the same sites with the same quantity of virus. The boosters were prepared essentially in the same manner as was the first injection, except that for the boosters the emulsification was done in incomplete Fruend's adjuvant.

One month later, each mouse was reimmunized subcutaneously with 100 micrograms of virus suspended in PBS. Each mouse was injected subcutaneously at the intersection of each limb with the trunk, and intraperitoneally. Three days after the last injection, the mice were sacrificed and their spleens were removed. The spleen cells were then fused with myeloma cells by the following procedure.

c) Fusion

Suspensions containing a five-to-one ratio of spleen cells to myeloma cells were prepared. The myeloma cells chosen were NS-1. The NS-1 cells were conditioned to have a doubling time about every seventeen hours. They were used for fusion when in the log phase. The NS-1 cells were subcultured in bacteriological plates (100 mm) at a concentration of $6 \times 10^4$ cells/ml in 10 ml of Dulbecco's Modified Eagle's Medium (DMEM) containing 5% Fetal Bovine Serum (FBS), 100 units/ml of penicillin and 100 micrograms/ml of streptomycin. The medium was changed every three days. Alternatively, the cells were subcultured at $1.54 \times 10^5$ cells/ml in 10 ml of the same medium, and the medium was changed every two days.

The spleen cells were prepared by placing the spleen on a bacteriological plate (100 mm) and injecting 20 ml of calcium magnesium free PBS (CMF-PBS) into both ends of the spleen to flush out the spleen cells. The flushed spleen cells were then transferred to a 50 ml centrifuge tube.

The spleen cells were centrifuged at 400 g for five minutes, and then suspended in 5 ml of 0.83% $NH_4Cl$ (0.155 M) for ten minutes at room temperature to lyse the erythrocytes. 5 ml of CMF-PBS was added to the tube to stop the lysis. The cells were then pelleted, and resuspended in 10 ml of CMF-PBS.

The concentration of lymphocytes was determined by adding 40 microliters of cell suspension to 10 ml of saline together with 3 drops of Zap-oglobin™. The number of lymphocytes was counted with a hemacytometer and from this value the concentration of cells was determined. The concentration was then multiplied by the dilution factor of 250 to yield the actual concentration of cells in the suspension.

The NS-1 cells were transferred from five of the bacteriological plates (100 mm) to a 50 ml centrifuge tube. The cell concentration was determined using the counting technique described above. $5 \times 10^7$ of the NS-1 cells were then suspended in 10 ml of CMF-PBS and mixed with $2.5 \times 10^8$ spleen cells in a 50 ml centrifuge tube.

The cells were spun down and washed once with 10 ml of CMF-PBS. The supernatant was aspirated as much as possible with a glass Pasteur pipette. The tube was gently tapped to free the cell pellet.

Prior to preparing the cells, a fusion mixture had been prepared as follows. 5 g of polyethylene glycol 1450 (purchased from Kodak) had been mixed with 5 ml of CMF-PBS and 0.5 ml of DMSO. This mixture had then been warmed to 56° C. to melt it, titrated to a final pH of 7.0, and filtered through a 0.22 micron Millipore filter in order to sterilize it. 1.0 ml aliquots had been added to Cryotubes, and these had been stored at $-70°$ C.

To prepare the fusion mixture for use, one of the aliquots in the Cryotubes was melted by heating it to 37° C. Separately, a tube containing 1-ml of DMEM (without serum) was heated to 37° C.

The 1.0 ml aliquot of polyethylene glycol fusion mixture was added to the cell suspension and the suspension was mixed well. Forty-five seconds after the polyethylene glcyol fusion mixture had been added, 2.0 ml of the pre-headed DMEM (without serum) was added dropwise with mixing. The remaining 8 ml of the pre-heated DMEM (without serum) was then added. The cells were left at room temperature for 10 minutes.

2.0 ml of FBS was added to the suspension and the suspensions were mixed well. The combination of the FBS and the DMB-PBS can help to prevent adherence of cells to the test tube walls. The suspensions were then centrifuged at 400 g for four minutes.

After having been spun down, the cells were suspended in 116 ml of a modified medium, supplemented with 5% FBS, 100 units/ml of penicillin, 100 micrograms/ml of streptomycin, and Littlefield's hypoxanthine, aminopterin and thymidine (HAT).

The concentration of the cell suspension was adjusted to $3.3 \times 10^5$ of the spleen cells per 200 microliters of suspension. 200 microliter aliquots of suspension were then distributed to each well of a 96 well microtiter plate. After seventeen such plates were prepared, the plates were transferred to an incubator and maintained at 37° C. in 5%$CO_2$.

The cells were grown for seven days in the plates, then the growth medium was withdrawn and new medium was added. Four days after that, the medium was again changed. Four days later, an enzyme linked immunosorbent assay (ELISA) was performed on the antibodies in the wells to determine which would bind the gp 120 protein of HIV-1. The ELISA was carried out as follows.

d) ELISA Procedure

Purified gp 120 protein was prepared as described in W.G. Robey, "Prospect for Prevention of Human Immunodeficienty Virus Infection: Purified 120-kD Envelope Glycoprotein Induces Neutralizing Antibody", *Proc Natl. Acad. Sci. USA* 83:7023–27 (1986). 50 microliters of a gp 120 suspension (at a concentration of 0.1 to 1.0 micrograms/ml) was added to wells of 96-well Immulon I plates with a twelve-channel pipette. The plates were covered and incubated for eighteen hours at 4° C., in order to allow the protein to bind to the plate.

The liquid contents of the plates were then emptied, and 200 microliters of 0.1 M $NH_4Cl$ was added to each well in order to saturate any remaining binding sites on the plates. The $NH_4Cl$ solution was left in the wells for thirty minutes at room temperature.

The $NH_4Cl$ solution was then removed and the wells were washed three times with PBS and 0.05% Tween 20. Some of the PBS/0.05% Tween 20 solution was left in the wells until the antibody suspension described below was added.

50 microliters of the cell fusion supernatant from each well of the seventeen 96 well plates was added to each of the wells on the Immulon I plates, and incubated for one hour. Following incubation, the plates were rinsed three times with PBS/0.05% Tween 20 in order to remove any unbound antibody.

The cell fusion supernatant will contain the antibody which is produced by the various hybridomas in the 96 well plates. The antibody which is specific to gp 120 will bind thereto. Inasmuch as the gp 120 is bound to the Immunlon I plate, the antibody specific to gp 120 will also become bound to the plate.

The next stage is to add the marker which will indicate the amount of bound antibody in each well. The marker chosen was horseradish peroxidase. This marker was conjugated with goat anti-mouse IgG to yield peroxidase-conjugated goat anti-mouse IgG. The goat anti-mouse IgG will bind to any mouse monoclonal antibody which is bound to the palte. The peroxidase marker can then be activated to indicate the quantity of bound antibody by an exzyme reaction.

The marker was added by adding to each well 100 microliters of the peroxidase-conjugated goat anti-mouse IgG diluted at 1:1000 in PBS/0.05% Tween 20 and 1% BSA. The plates were incubated for one hour at room temperature. Thereafter, the plates were washed three times with PBS/0.05% Tween 20 to remove any unbound goat anti-mouse IgG conjugate.

The next step is to activate the peroxidase marker which is conjugated to the goat anti-mouse IgG. This is done by adding 200 microliters of 3', 3', 5', 5' tetramethyl benzidine substrate solution to each well, and incubating at room temperature for 30 minutes. The color reaction is stopped by adding 50 microliters of 2.0 M $H_2SO_4$.

The intensity of color was determined with an ELISA reader at 450 nm. The amount of antibody specific to gp 120 is proportional to the intensity of the color.

It was found that there were approximately 200 wells in the 96 well microtiter plates which produced antibodies which bound to gp 120 to at least some extent. Of these 200 wells the 39 which produced antibody showing the highest color intensity were selected for another screening step.

e) Immunofluorescence Assay Using Live T-Cells

An immunofluorescence assay was performed to determine whether any of the antibodies which were reactive with gp 120 in the ELISA would bind spe- cifically to live HIV-1 infected H9 cells. The H9 cell line is permissive to persistent infection by HIV-1. This cell line was obtained from the American Type culture Collection in Rockville, Md. Antibody which binds to infected cells, but not uninfected cells, is probably selective to a domain of the HIV-1 envelope protein on the extracellular side of the cell membrane. The immunofluorescence assay helps to select those gp 120 reactive antibodies which have a high potential to recognize the neutralization epitopes on the HIV-1 virion, and to inhibit syncytium formation by infected T-cells.

Cultures of infected H9 cells were maintained as described above under the heading "Preparation of Virus". The procedure by which the assay was performed is described below.

(i) Assay Procedure 50 microliter aliquots of infected H9 cell suspension at a concentration of $5\times10^6$ cells/ml was added to each of thirty-nine 1.5 ml microfuge tubes. 50 microliter aliquots of the supernatant from the 39 wells containing the ELISA positive clones was then added to each tube. The antibodies in the supernatant which react with H9 cells will bind to any H9 cells which are in the tube.

The tubes were then incubated for thirty minutes at room temperature. After incubation, the tubes were spun, the supernatant was withdrawn, and the cells were washed three times with a mixture of RPMI 1640, containing 2% fetal calf serum and 0.1% sodium azide. The tubes were then tapped to loosen the cell pellet.

10 microliters of labeled antibody, goat anti-mouse IgG conjugated with fluorescein isothio-cyanate (FITC), was added to each test tube at a dilution of 1 to 200. This labeled antibody will bind to any monoclonal antibodies which have attached to HIV-1 infected H9 cells and provide a means for identifying these monoclonal antibodies.

The tubes were again incubated for thirty minutes at room temperature. The tubes were centrifuged, and the cells were washed with the same medium as before. The cells were then resuspended in PBS, placed onto individual slides and cover-slipped. The cells were viewed with a fluorescence microscope.

To determine which of the thirty-nine selected wells contained antibodies which bound to uninfected H9 cells, an essentially identical procedure as described above was performed, using infected H9 cells instead.

(ii) Results

Seven of the thirty-nine wells tested contained clones which produced monoclonal antibodies binding to live infected H9 cells but not to uninfected H9 cells. That is, when using antibodies from these seven wells the infected cells fluoresced, but the uninfected cells did not.

Cells and antibodies from the seven wells which contained immunofluorescence positive clones were collected. Two of these hybridoma cell lines, which secrete the monoclonal antibodies BAT123 and BAT123, have been deposited at the American Type Culture Collection in Rockville, Md. under Accession numbers HB 10438 and HB 10626, respectively, on the dates Apr. 2, 1990 and Dec. 14, 1990, respectively, and are available for inspection by the Patent and Trademark Office during the pendency of this application.

f) Single Cell Cloning

Cell suspensions from each of the thirty-nine ELISA positive wells were expanded in the wells of a twenty-four well plate. After five days of growth in the twenty-four well plate, the cell suspension from the seven wells tested immunoreactive to infected H9 cells which were diluted to thirty, fifty and one hundred cells per milliliter. 0.1 ml of the diluted cell suspensions (containing an average of three, five and ten clones, respectively) was placed into the wells of a nine-six well plate. The wells had previously been coated with histone.

After each cell grew up to become a colony, the cells were checked under a microscope. The cells of each colony did not move about and form satellite colonies. The single-cell clone from each of the seven clonings showing strongest reactivities in ELISA and immunofluorescence was chosen and expanded in culture.

g) Sodium Dodecyl-Sulfate Polyacrylamide Gel Electrophoresis (SDS-PAGE) and Western Blot Procedure In Western blot analysis, the virus is solubilized into its component proteins. The clones which produce monoclonal antibodies binding to the exterior envelope protein of HIV-1 (gp 120) are the ones which are desired. The procedure is described below.

30 micrograms of HIV-1 was solubilized by heating it in a sample buffer (which contained 2% SDS and 5% beta-mercaptoethanol) at 100° C. for five minutes. It was then loaded onto a 12% slab polyacrylamide gels 1.5 mm thick. The gel was run at constant voltage of 35 mV for 8 hours at room temperature. The procedure was described in "Procedure for Preparation of Gels for Western Blot Detection of HTLV-III Antibodies", published by Biotech Research Laboratories, Inc., Rockville, Md. The protein bands were transferred onto nitrocellulose paper by setting the power at 30 volts (about 0.1A) and running for 16 hours at room temperature. The next morning, the voltage was increased to 60 volts (about 0.2A) and the transfer was run for 1–2 hours to maximize the transfer of gp 120 and gp 160. The transfer buffer contained 24 g of Tris base, 57.6 g of glycine and 800 ml of methanol. Water was added to make the solution up to 4 liters.

The nitrocellulose sheets were then rinsed with PBS/ 0.05% Tween 20 and placed in a tray containing Blotto buffer. The tray was gently shaken for two hours at room temperature. Blotto buffer consists of 50 g of non-fat dry milk, 1.0 g of antifoam A (optional), 0.1 g of merthiolate, and sufficient PBS to make a final volume of 1.0 liter. The buffer pH was adjusted to 7.0.

The nitrocellulose sheets where then rinsed in PBS/0.05% Tween 20 and dried on a paper towel between weighted plexiglass plates. The nitrocellulose sheets were then cut into strips 0.5 cm wide, each of which was numbered consecutively. The strips can either be used immediately or stored dry and in the dark for up to one month. The strips which carry the gp 120 band were to be used in the next stage.

The gp 120 nitrocellulose strips were then prepared to allow binding of monoclonal antibody to the protein bands. Forty of these strips were individually placed into an assigned slot of a slot tray and pre-soaked for twenty minutes in PBS/0.3% Tween 20. The pre-soak solution was aspirated into a Clorox™ containing trap. The strip wells was then rinsed once with PBS/0.05% Tween 20, the tray was shaken several times, and the solution was aspirated off.

The positive control was made of 2.0 ml of Blotto buffer/4% goat serum (which is made by mixing 100 ml of Blotto buffer and 4 ml of heat inactivated normal goat serum) added to one strip after which 10 microliters of heat inactivated AIDS patient serum was added to the well. 2.0 ml of supernatant was withdrawn from each of the thirty-nine wells in the microtiter plates which contained ELISA positive clones. Mixtures were made which consisted of 2.0 ml of supernatant, 5% non-fat dry milk, 50 microliters of 1 M HEPES (pH 8.0), and merthiolate.

An aliquot of suspension was added into each strip well containing a strip. The mixture was then aspirated into a Clorox™ containing trap. The strips wells were rinsed once with PBS/0.05% Tween 20, rocked several times by hand, and aspirated with wash buffer. The strips were then washed three times with PBS/0.05% Tween 20, allowing five minutes for each rinse.

The strips were then reacted with the staining reagents, which permit visualization of specific antibody binding to gp 120. The reagent chosen was horseradish-peroxidase. This reagent exhibits color when contacted by a working substrate which consists of 10 ml of PBS, pH 7.4, 2.0 ml of substrate stock, and 4.0 microliters of 30% $H_2O_2$. Substrate stock is made by dissolving 0.3 g of 4-chloro-1-napthol in 100 ml of anhydrous methanol.

2.0 ml of Blotto/4% goat serum, containing 1:100 biotinylated goat anti-mouse IgG, was then added to each strip well. The trays were incubated at room temperature for thirty minutes on a rocking platform. The goat anti-mouse IgG conjugate will, of course, bind to any monoclonal antibody which has bound to the gp 120 on a strip.

The strip wells were then rinsed once with PBS/0.05% Tween 20, and shaken by hand several times to remove excess goat anti-mouse IgG conjugate. The wash buffer was discarded. The strip wells were then washed three times with PBS/0.05% Tween 20. Each washing lasted for five minutes.

2.0 ml of Blotto/4% goat serum containing 1:1000 horseradish-peroxidase-avidin D conjugate was added to each strip well. The avidin in this conjugate binds to the biotin in the goat anti-mouse IgG conjugate. Therefore the horseradish-peroxidase marker becomes linked to goat anti-mouse IgG and thereby marks any bound antibody. Following addition of the conjugate, the trays were incubated for thirty minutes at room temperature on a rocking platform.

Each strip well was washed three times with PBS/0.05% Tween 20, five minutes per wash, then once with PBS. 2.0 ml of the working enzyme substrate was added to each well, and the trays were incubated at room temperature until color developed. The working substrate solution contained 0.05% 4-chloro-1-naphthol and 0.01% $H_2O_2$ in phosphate buffer saline at pH 7.4.

(iii) Results

As discussed above, the Western blot analysis was performed using antibody from the thirty-nine ELISA positive wells. With Western blot analysis only antibody from six of these thirty-nine wells was found to react with gp 120. All six of these wells were among the seven wells which had been found immunofluorescence positive in the immunofluorescence assay. Thus, only one of the seven immunofluorescence positive clones was not also positive in Western blot analysis.

h) Production and Purification of Monoclonal Antibodies

To produce large quantities of desired monoclonal antibodies, the following procedure was performed.

The seven immunofluorescence positive clones, which have situated in the wells in the second twenty-four well plate, were grown up in a 100 mm tissue culture plate. The expanded culture of the selected seven single-cell clones were then separately injected into the peritoneal cavity of pristane treated mice, using five million cells per mouse. After seven days the ascites fluid of each mouse was collected and frozen.

The monoclonal antibodies in the ascites fluid were purified as follows. The frozen ascites fluid was thawed and filtered through a nylon cloth to remove viscous material. Sufficient phenylmethyl sulfonyl fluoride was added to the ascite fluid so that there was a final concentration of 0.1 mM. 0.05 ml of 1.2M acetate buffer (pH 4.0) was added for every milliliter of ascites fluid. The final concentration of the acetate buffer was 60 mM. The pH was adjusted to 4.5.

For every milliliter of treated ascites fluid, 25 microliters of caprylic acid (MW of 144.21, density of 0.91) was added dropwise with vigorous stirring. The suspension was kept at room temperature and stirred continuously for 30 more minutes.

The suspension was then centrifuged at 15,000 g for ten minutes in order to remove the precipitate. The supernatant, which contains IgG, was neutralized by adding a volume of 1 M HEPES buffer (pH 8.0) equal to one-tenth the volume of the supernatant. The IgG was then precipitated with 50% $(NH_4)_2SO_4$.

The precipitate was then dissolved in HEPES saline buffer. This solution was dialysed overnight against HEPES saline buffer in order to remove $(NH_4)_2SO_4$ from the IgG. The HEPES saline buffer was changed twice during the dialysis. After dialysis, the HEPES buffer saline contains purified dissolved IgG. The purified IgG was used in the infectivity assays and the syncytium formation assays which follow.

Example II
Verifying the Efficacy of the Invention a) Neutralization Assay

An assay was performed to determine the effectiveness of the monoclonal antibodies of the invention in inhibiting infection of T-cells by HIV-1 virion. A comparison was made of the number of cells infected when HIV-1 alone was added to a cell culture, with the number infected when HIV-1 and the monoclonal antibodies of the invention were added. The cells selected for the neutralization assay were the H9 clones of the HT cell line.

i) Preparing the Virus, Antibody and Cells

H9 cells were prepared by washing a cell culture with H9 growth medium. The H9 growth medium contained 20% FBS (heat inactivated) in RPMI 1640, 5 mM of L-glutamine, 50 units/ml of penicillin, 50 mg/ml of streptomycin, and 5 mM of HEPES. The cells were then resuspended to a final concentration of $2 \times 10^6$ cells/ml. The suspension was then incubated with 2 micrograms/ml of polybrene in a water bath at 37° for twenty minutes.

After incubation, the cells were spun down at 700 g for seven minutes. The supernatant was then discarded, and the cells were resuspended in H9 growth medium and washed again to remove the polybrene. The cells were then resuspended to $2 \times 10^6$ cells/ml in growth medium.

Six of the seven immunofluorescence positive clones were chosen for use in the neutralization assay. The antibodies from the purified ascites (as described above) were sterilized by passing them through a 0.22 micron Millipore filter. The solution was then diluted in the H9 growth medium to yield different final concentrations of 100, 10, 1, 0.1, and 0.01 micrograms/ml.

Virus at 20 $TCID_{50}$, or twenty times the $TCID_{50}$ value, was used in the infection of H9 cells. The TCID50 value of the virus preparation was determined in previous infectivity assays under the same experimental conditions. It is defined as the virus titer at which 50% of the experimental wells are infected. 20 $TCID_{50}$ was equivalent to roughly a $4.72 \times 10^{-5}$ dilution of the viral stock.

In the infectivity assays, 30 microliters of virus suspension, and 30 microliters of each of the antibody solutions, were mixed in the wells of a microtiter plate at 4° C. for one hour. Each well was done in duplicate. The plate was then warmed in an incubator at 37° C. and 5% $CO_2$ for thirty minutes. 30 microliters of the polybrene treated H9 cell suspensions was then added to each well.

The microtiter plates were then incubated for one hour at 37° C. in an incubator. 110 microliters of the growth medium was added to each well, bringing the total volume to 200 microliters. The plates were incubated for three days, and new growth medium was replaced every three days. Cells were collected on the third, sixth, ninth and thirteenth day.

The identical procedure described above was also performed using murine monoclonal antibody to human chorionic gonadotropin (anti-HcG) rather than one of the anti-HIV-1 antibodies of the invention. The cells treated with the anti-HCG antibody served as a negative control.

ii) Immunofluorescence Assay of Infected Cells 100 microliter aliquots of the cell suspensions collected on days 9 and 13 were washed with 3 ml of PBS. The cell suspension was centriguted at 700 g for seven minutes and was washed again in PBS. The cells were finally resuspended in 50 microliters of PBS and 10 microliters of suspension was dotted onto a glass slide. This suspensions were air dried and then fixed with 1:1 acetone/methanol for ten minutes, air dried and stored at −20° C. before assay.

In the assay, the fixed cells were rehydrated in PBS for twenty minutes and then incubated with 5% normal goat serum in PBS for another thirty minutes. After dripping away the excess normal goat serum, the cells were incubated at room temperature for one hour with anti-p24 monoclonal antibody (at a dilution of 1:100) containing 2% normal goat serum. This antibody binds specifically to the p24 core protein of HIV-1. The slides were kept in the humidifier to avoid drying. After the incubation, the slides were rinsed for three times in PBS for a total of 30 minutes. Then fluorescein conjugated goat anti-mouse IgG (F(ab')$_2$) fragment was added at a dilution of 1:20. The slides were incubated for one hour at room temperature. The slides were then rinsed in three changes of PBS for thirty minutes and counterstained with 0.5% Evans blue for five minutes, washed and mounted in Fluoromount G. The cells were then observed under a fluorescence microscope.

The number of infected cells were counted at the magnification of 400x. Four data points were collected from each slide by random sampling over the field.

iii) Results

Figure 2:
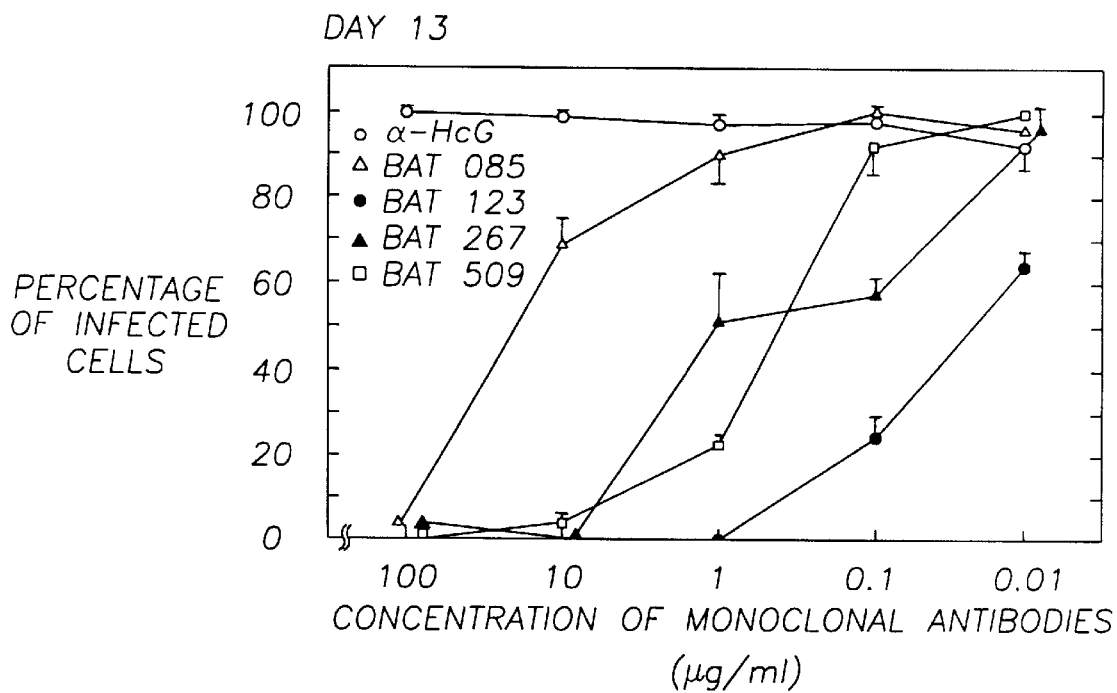

The results are depicted graphically in FIGS. 1 and 2, where the percentage of immunofluorescence cells is plotted against the concentration of antibody in suspension. The results in FIG. 1 are from cells collected on day 9. In FIG. 2 the cells were collected on day 13.

Turning to FIGS. 1 and 2, it can be seen that four of the six antibodies tested (designated as BAT 123, 267, 509, and 085) were effective in inhibiting infection. In particular, BAT123 showed almost complete inhibition of infection on day 9. This results is to be contrasted with the negative control anti-HcG antibody, which exhibited virtually no inhibition. Nearly 100% of the cells treated with anti-HcG were immunofluorescent, irrespective of the concentration of antibody. The similar result was obtained with monoclonal antibody BAT 496 which is reactive with gp 120 but shows no neutralization activity. For this reason, BAT 496 was not assayed on day 13 and does not appear in FIG. 2.

It should be noted that another antibody, BAT401, was tested for neutralization. However, the results do not appear in FIGS. 1 and 2 because it was found less effective in syncytium formation inhibition.

A comparison of FIGS. 1 and 2 shows that as time goes on, more of the cells in the suspension become infected. This result is expected. The amount of antibody in suspension available to neutralize the virus is decreasing due to change in medium and probably degradation or internalization. However, the infected H9 cells continually produce more virus, and this virus eventually infects all the cells.

The plots in FIGS. 1 and 2 show that with a decreasing concentration of antibody, a greater number of cells are infected. This indicates that the neutralizing effect of the antibodies is dosage dependent. The $IC_{50}$ value of each monoclonal antibody, which is the dosage at which 50% of the cells are infected, was calculated. The results as taken on day 9 appear below in Table I.

TABLE I

| Monoclonal Antibodies | $IC_{50}$ |
|---|---|
| Anti-HcG (Negative Control) | $1 \times 10^5$ ng/ml |
| BAT085 | 100 ng/ml |
| BAT123 | 10 ng/ml |
| BAT267 | 10 ng/ml |
| BAT509 | 30 ng/ml |
| BAT496 | $1 \times 10^5$ ng/ml |

It can be seen that the monoclonal antibodies which are most effective at inhibition (BAT 123, 267 and 509), do so in nanogram quantities. This indicates that these monoclonal antibodies may also be very effective in minute quanitities for in vivo AIDS therapy. The use of such minute doses would be a significant advantage over known therapeutic agents.

b) Inhibition of Syncytium Formation

Another test for the monoclonal antibodies of the invention was to determine whether they inhibited syncytium formation. Inhibition of syncytium formation would enhance the therapeutic value of the antibodies, inasmuch as the majority of cell infection and cell death in vivo is believed to occur via syncytium.

The syncytium assay was based on the assumption that the exterior envelope protein of the virus in infected H9 cells binds to the CD4 antigen which is carried by T cells. In the assay, infected H9 cells are added to a well containing CD4 DNA transfected HeLa cells. HeLa cells are used because they adhere, in a monolayer, to the bottom of the well. These transfected HeLa cells express abundantly CD4 antigen on their cell surface. Thus, they have the ability to fuse with infected H9 cells. Therefore, if syncytium formation occurs, aggregates of HeLa and H9 cells will be bound to the well. These multi-nucleated giant cells can readily be observed and counted.

The protocol for the syncytium formation assay is set forth below.

(i) Procedure for Syncytium Formation Assay

HeLa T4 cells (which express the CD4 antigen on the surface) were grown in a HeLa-T4 growth medium, which contained 5% FBS (heat inactivated) in DMEM, 5mM L-glutamine, 50 units/ml of penicillin, 50 mg/ml of streptomycin, and 5 mM of HEPES. The cells were harvested by trypsinization, to remove the cells from the flask, and washed. The cells were then seeded onto a 96 wells microtiter plate at a density of 10,000 cells per well. The plates were incubated at 37° C. for thirty-six hours until 90% confluency was reached.

Both infected and uninfected H9 cells were then prepared. For preparing these cells, the cell suspension was first washed twice with H9 growth medium (20% FBS in RPMI 1640, 5 mM of L-glutamine, 50 units/ml of penicillin, 50 mg/ml of streptomycin and 5 mM of HEPES.) The cells were then resuspended in HeLa-T4 at a concentration of 0.4 million/ml.

The antibodies were prepared by first performing a sterile filtration on the seven antibody solutions which had been used in the neutralization assay. Six of these solutions contained antibodies of the invention, and the seventh contained the anti-HcG. Each solution was then diluted to make two final concentration of 1.0 and 10 micrograms/ml.

50 microliters of each antibody solution and 50 microliters of infected H9 cell suspension was added to the various wells of the microtiter plate. The microtiter plate wells had previously been coated with the HeLa T4 cells. In another HeLa T4-coated well, infected H9 cell suspension was added without the addition of antibody. This well was to serve as a positive control. In yet another coated well, uninfected H9 cell suspension was added. This well was to serve as a negative control. The experiments were done in triplicate.

The plates were then incubated for eighteen hours at 37° C. and 5% $CO_2$. The plates were washed gently twice with DMEM in order to remove unattached H9 cells. The DMEM was removed and the cells were fixed by adding 200 microliters of methanol per well for seven minutes. After removing the methanol, the cells were air dried, and then stained with 100 microliters of 1.4% methylene blue for ten minutes. The cells were rinsed with distilled water three times.

After staining, the cells were then observed under an inverted microscope (at a magnification of 100 times), and the number of syncytia per field was determined. Aggregates of cells were considered to be a syncytium if more than five nuclei were present. Each well was counted three time randomly.

(ii) Results

The negative control well showed no syncytium formation. The results for the remainder of the wells appear below in Table II, expressed as a mean +standard deviation.

TABLE II

Inhibition of Syncytium Formation Between HIV-infected H9 Cells and HeLa T₄ Cells

| Antibody* & Concentration | | Number of Syncytia per Field | % Inhibition |
| --- | --- | --- | --- |
| None | | 54.8 ± 3.6 | 0 |
| Anti-HcG | 1 | 50.0 ± 5.1 | 8.7** |
| | 10 | 54.7 ± 7.6 | 0 |
| BAT085 | 1 | 39.7 ± 2.8 | 27.6 |
| | 10 | 41.3 ± 6 | 24.6 |
| BAT123 | 1 | 30.3 ± 4.5 | 44.7 |
| | 10 | 15.3 ± 4.7 | 72.0 |
| BAT267 | 1 | 41.0 ± 6.6 | 25.2 |
| | 10 | 27.3 ± 5.7 | 50.2 |
| BAT509 | 1 | 41.7 ± 4.9 | 23.9 |
| | 10 | 28.3 ± 3.3 | 48.5 |
| BAT496 | 1 | 56.3 ± 9 | 0 |
| | 10 | 52.0 ± 3.6 | 5.1** |

*The 1.0 microgram/ml and the 10 microgram/ml solutions of antibody are designated "1" and "10" respectively.
**Not significantly different from negative control.

It can be seen from Table II that these results suggest that screening by the above-described methods is essential to identify the best antibodies for therapeutic use. The same antibodies which lowered infectivity of free HIV-1 virions (as shown in FIGS. 1 and 2) also were effective in inhibiting syncytium formation. BAT 123, 267 and 509 were particularly effective in both applications. BAT 496 was almost ineffective in both applications as was, of course, the negative control anti-HcG. Although BAT 085 was effective in neutralization, it was not among the most effective in syncytium inhibition.

BAT401 was not very effective at syncytium inhibition, although it was effective in the neutralization assay. This result indicates that antibodies which are effective in inhibiting HIV-1 infection are not necessarily effective in inhibiting syncytia formation. Accordingly, the three monoclonal antibodies of invention which were most effective (BAT123, 264 and 509) at inhibiting both infectivity by the HIV-1 virions and syncytium formation, were deposited at the American Type Culture Collection in Rockville, Md. They are available for inspection by the Patent and Trademark Office during the pendency of this application.

The Table II results demonstrate that, similar to neutralization as shown in Table I, syncytium inhibition is also dosage-dependent. The solutions with 10 microgram/ml of antibody were generally more effective in inhibition than the 1 microgram/ml solutions.

Example III
Neutralization of Different Strains and Isolates of HIV-1

Several antibodies were found to inhibit the infectivity of free HIV-1 virions and the syncytium formation between HeLa-CD4+cells and H9 cells infected by HIV-1B. Since genomic analyses indicate that the virus mutates significantly both in vivo and in vitro (Alizon, M., Wain-Hobson, S., Montagnier, L. and Sonigo, P. (1986) *Cell* 46:63–74; Starcich, B.R., Hahn, B.H., Shaw, G.M., McNeely, P.D., Modrow, S., Wolf, H., Parks, E.S., Parks, W.P., Josephs, S.F., Gallo, R.C. and Wong-Staal, F. (1986) *Cell* 45:637–648), the application of these neutralizing monoclonal antibodies as agents for therapy and protection relies heavily on whether they are group-specific and protect HIV-1 infection caused by a large proportion of strains of the virus in the population. It is important to know whether BAT 123 and the other neutralizing monoclonal antibodies we raised recognize one or more distinct neutralization epitopes in the viral envelope protein gp120 with conserved amino acid sequences among different strains of HIV-1. In order to understand these characteristics of the antibodies, we studied whether these antibodies can inhibit the syncytium formation by other strains of HIV-1 with a substantial degree of heterogeneity in the amino acid sequence of gp120 (RF, AL, MN, Z84 and Z34) (Starcich et al., supra.). The neutralization antibody BAT 123 was chosen in the study because it was shown to elicit highest potency in the neutralization of the virus. In order to evaluate the effectiveness of the neutralizing antibodies on different HIV-1 variants existing in the infected population, we collected blood specimen randomly from infected individuals (in Houston, Tex.; in Los Angeles, Calif.; and in Boston, Mass.) with different disease states, and examined the effect of BAT 123 on the viral infection in the lymphocyte preparations by co-culture experiments.

a) Syncytium formation assay

Syncytium formation assay was performed as described in Example 2.

b) Co-culture assay

The procedure used is similar to that described earlier, 30 ml of heparinized blood from each patient was freshly collected and processed for mononuclear leukocytes by density-gradient centrifugation. Briefly, the whole blood was diluted with equal volume of phosphate-buffered saline (PBS). 25 ml of the diluted blood was laid over 10 ml of Ficoll-Paque (Pharmacia) and centrifuged at 1500× g for 30 minutes; at the end of the centrifugation, the interphase containing mononuclear leukocytes was removed and washed twice in PBS. The mononuclear leukocytes were then cultured at $0.5-1\times10^6$/ml in the RPMI 1640 medium supplemented with 15% heat-activated fetal bovine serum, 2mM L-glutamine, 10% interleukin-2 (Cellular Products), 25 neutralizing units/ml sheep anti-human alpha interferon (Interferon Science), 100 units/ml penicillin, 100 ug/ml streptomycin and 2 ug/ml Polybrene. Equal volume of phytohaemagglutinin (PHA)-stimulated mononuclear leukocytes from normal donor blood was mixed with the patient culture. The mononuclear leukocytes from the normal donor blood was stimulated for one day early with 2 ug/ml PHA-P (Sigma). They were washed twice in PBS to remove the lectin. BAT 123 was added to the test culture at the final concentration of 10 ug/ml. The total volume of the culture was 10 ml. Five ml of the cell culture was removed at 3–4 day intervals, centrifuged at 1,500× g for 15 minutes to remove the cells and debris. The supernatants were collected and assayed for reverse transcriptase activities after precipitation of the virus using 10% polyethylene glycol (PEG) (Gupta, P., Galachandran, R., Grovit, K., Webster, D. and Rinaldi, C. Jr. (1987) *J. Clin. Microbiology* 25:1122–1125).

c) Reverse transcriptase assay

The procedure for the measurement of reverse transcriptase activity was described earlier (Barre-Sinoussi, F., Chermann, J.C., Rey, F. Nugeyre, M.T., Charmaret, S., Gruest, J., Daugnet, C. Axler-Blin, C., Vezinet-Brun, F., Ronziou, C., (1984) *Science* 220:86–87). Briefly, the PEG-precipitated virus was solubilized for 20 minutes in 100 ul of Tris-buffered saline (pH 8.2) containing 0.1% Triton X-100, 2 mM dithiothreitol, 0.2mM leupeptin and 50 mM -amino-n-caproic acid. In the assay, 100 ul of the substrate solution in 50 mM Tris-HCl pH 8.2 containing 8mM $MgCl_2$, 20 uCi $^3$H-thymidine triphosphate (2mCi/ml), 0.05 units of template-primer poly(rA).p(dT) $_{12-18}$ was added to 25 ul of the solubilized virus. No template-primer was added to the corresponding control, but substituted with distilled water instead. The reaction mixtures were incubated at 37° C. for one hour and the reaction was terminated by addition of 5% cold trichloracetic acid and finally filtered over Whatman GF/C filters which were washed thoroughly and counted for radioactivity using a scintillation counter. The specific reverse transcriptase activities were calculated as the difference in radioactivity when the template-primer was added.

Results & Discussion

We studied the neutralizing monoclonal antibodies claimed with regard to their group-specificity to the virus and their cross-protection to six different HIV-1 strains (HIV-$1_B$, HIV-$1_{RF}$, HIV-$1_{AL}$, HIV-$1_{MN}$, HIV-$1_{z84}$, and HIV-$1_{z34}$). In syncytium formation assay between HeLa-CD4+ cells and H9 cells chronically infected with these strains of HIV-1 respectively, BAT 123 at 25 ug/ml inhibited syncytium formation by almost 80%. It also reduced the syncytium formation of H9 cells infected with HIV-$1_{MN}$, HIV-$1_{AL}$, HIV-$1_{RF}$ and HIV-$1_{Z34}$ by approximately 50%, and HIV-$1_{z84}$ by 23%. (See Table III).

TABLE III

CROSS-PROTECTION OF SYNCYTIUM FORMATION BY
H9 CELLS INFECTED WITH DIFFERENT HIV-1 STRAINS

| Infected H9 Cells Inhibition | With Antibody | Without Antibody | % of |
|---|---|---|---|
| H9 uninfected (control) | — | — | — |
| H9 - HIV - $1_B$ | 2.33 ± 0.51* | 10.25 ± 0.99 | 77.3 |
| - HIV - $1_{MN}$ | 2.08 ± 0.38 | 4.25 ± 0.46 | 51.0 |
| - HIV - $1_{AL}$ | 7.08 ± 0.66 | 13.91 ± 1.27 | 49.1 |
| - HIV - $1_{RF}$ | 1.91 ± 0.55 | 3.91 ± 0.47 | 51.0 |
| - HIV - $1_{Z84}$ | 12.41 ± 1.46 | 16.08 ± 0.55 | 22.8 |
| - HIV - $1_{Z34}$ | 1.58 ± 0.14 | 3.08 ± 0.55 | 48.7 |

*Expressed as number of syncytia per microscopical field (x ± S.E., n = 11 or 12), p 0.05, paired student's t test.

In the co-culture experiments using lymphocytes isolated from the peripheral blood of patient clinically diagnosed positive asymptomatic state, AIDS or ARC; out of 32 patient blood specimen tested, the virus had been isolated from 18 samples as measured for reverse transcriptase activities. When 10 ug/ml BAT 123 was added in the culture medium throughout the experiments, the viral replication was inhibited in all of the 18 virus-positive cultures. The degree of inhibition ranged from 43.7 to 100%. Among the 18 samples, 8 samples were effectively inhibited by over than 90%. (See Table IV).

The results from our in vitro experiments suggest that the neutralizing monoclonal antibody BAT 123 is group-specific and can cross-protect different diverse strains of HIV-1 in the syncytium formation assays and inhibit viral infection in patient blood specimen. (See Table IV).

TABLE IV

CO-CULTURE EXPERIMENTS
Reverse Transcriptase Activity (cpm)

| Patient No. | Control | With BAT 123 | Percent Inhibition | T4 Cell Count/μl | Total Lymphocyte/μl | Clinical States |
|---|---|---|---|---|---|---|
| 7 | 720123 | 335156 | 53.4 | 180 | 2250 | +, asym |
| 8 | N.D.* | | | 398 | 1443 | ARC |
| 9 | N.D. | | | 180 | 2178 | +, asym |
| 10 | 100825 | 38283 | 62.0 | 0 | 5044 | AIDS (PCP) |
| 11 | 331689 | 186660 | 43.7 | 110 | 2210 | AIDS (PCP) |
| 12 | 317107 | 104 | 99.9 | 14 | 462 | AIDS (PCP, KS) |
| 13 | N.D. | | | 261 | 1440 | ARC |
| 14 | N.D. | | | 23 | 2310 | AIDS (PCP) |
| 15 | 9081 | 0 | 100.0 | 229 | 1590 | AIDS (PCP) |
| 16 | 66224 | 14382 | 72.4 | 29 | 400 | AIDS (PCP) |
| 17 | 65991 | 5593 | 91.5 | 25 | 2553 | ARC |
| 18 | N.D. | | | 715 | 3502 | ARC |
| 19 | N.D. | | | 825 | 2886 | +, asym |
| 20 | N.D. | | | 948 | 2964 | ARC |
| 21 | N.D. | | | 151 | 1892 | ARC |
| 22 | 22034 | 829 | 96.2 | 171 | 2444 | AIDS (PCP) |
| 23 | 76103 | 1004 | 98.6 | 140 | 870 | AIDS (PCP) |
| 24 | N.D. | | | 503 | 2400 | +, asym |
| 25 | 166167 | 10900 | 93.4 | 163 | 3264 | AIDS (PCP) |
| 26 | 171670 | 66576 | 61.2 | 74 | 530 | +, asym |
| 27 | 293485 | 143301 | 51.1 | 8 | 2016 | AIDS |
| 28 | 16884 | 146 | 99.1 | 33 | 1050 | AIDS |
| 29 | 38703 | 9104 | 76.0 | 197 | 1364 | AIDS |
| 30 | 20863 | 1298 | 93.8 | 178 | 3570 | AIDS |
| 31 | N.D. | | | 168 | 2808 | AIDS |
| 32 | 284570 | 102787 | 63.9 | 265 | 3716 | AIDS |
| 33 | N.D. | | | 30 | 594 | AIDS |
| 34 | Blood not processed** | | | 33 | 1664 | AIDS |
| 35 | N.D. | | | 721 | 4200 | +, asym |
| 36 | N.D. | | | 723 | 2784 | +, asym |

TABLE IV-continued

CO-CULTURE EXPERIMENTS
Reverse Transcriptase Activity (cpm)

| Patient No. | Control | With BAT 123 | Percent Inhibition | T4 Cell Count/µl | Total Lym- phocyte/µl | Clinical States |
|---|---|---|---|---|---|---|
| 37 | 43108 | 14062 | 67.4 | 42 | 4355 | +, asym |
| 38 | N.D. |  |  | 516 | 3036 | +, asym |
| 39 | 50256 | 8019 | 84.0 | 10 | 350 | AIDS |

* N.D. = Not detected
** Specimen from VA-34 was not processed since there was not enough blood.
asym = asymptomatic
AIDS = acquired immunodeficiency syndrome
ARC = AIDS related complex
PCP = Pneumocystic carinii pneumonia
KS = Kaposi's sarcoma

EXAMPLE IV

Determining The Peptidic Segments Of Gp120 Reactive With Monoclonal Antibodies

Methods

In order to map the epitopes on gp12o of HIV-1 that are recognized by the monoclonal antibodies, we have determined using Western blot assays the reactivities of some of the monoclonal strips. The strips were obtained from Dr. Steve Petteway, Medical Products Department, DuPont de Nemours and Company, Wilmington, Del. The synthetic peptides on the strips are 8–20 amino acid residue long. These peptides represent overlapping peptidic segments across the entire length of gp120 of HIV-IB strain. Several tens of peptide solutions had been adsorbed on individual strips in equally spaced regions and the strips were provided to us in a dry form.

The immunoblotting procedure using the nitro-cellulose strips is the same as the Western blot procedure used to determine whether the monoclonal antibodies react with gp120 described in the preceding section.

Results

Three of the monoclonal antibodies BAT123, BAT267, and BAT085 showed very clear and specific reactivities with particular peptides in the Western blot assay.

| BAT267 | RPNNNTRKRIRIQRG | (residue #298–312) |
|---|---|---|
| BAT123 | RIQRGPGRAFVTIGK | (residue #308–322) |
| BAT085 | VQKEYAFFYKLDIIP | (residue #178–192) |

The 15 amino acid long peptides reactive with BAT267 and BAT123 overlap by 5 amino acids. However, the antibodies react with just one of them and do not react with the other to any measurable extent. The antibodies do not react with peptides overlapping at the other ends either, i.e. BAT267 does not react with LNQSVRINCTRPNNN and BAT123 does not react with VTIGKIGNMRQAHCN. These results suggest that the antibodies react with an epitope borne by either all or a part of the middle five amino acids or a combination of these amino acids with some of the flanking amino acids. Similar findings have been made for BAT085 and similar conclusions may be made for it.

Example V

Immunotoxins with HIV Neutralizing Monoclonal Antibodies a) Methods

Antibodies: Murine monoclonal antibody (MoAb) G3.519 (IgGI) binds to a conserved region in or near the CD4 receptor binding site on gp120 and is known to have neutralizing activities against diverse strains of HIV-1. See U.S. Pat. application Ser. No. 07/137,861, entitled "Monoclonal Antibodies Which Neutralize HIV-1 Infection and Their Applications in Therapy and Prevention for AIDS", Chang, Attorney's Docket No. TNX87-11A, the teachings of which are incorporated by reference herein. MoAb BAT123 (IgG1) recognizes a relatively variable peptidic segment in gp120 and exhibits effective neutralizing activity against HTLV-IIIB strain. The details of its neutralizing activity are described above. MoAbs were produced in ascitic fluids of CAF1 mice bearing the hybrihybridomas and purified by protein A affinity chromatography.

Purification of PAP-S: PAP-S was purified from seeds of *Phytolacca americana* (pokeweed) using a method of Barbieri et al. (L. Barbieri, et al., *Biochem J.*, 203: 55–59 (1982)). Briefly, pokeweed seeds (100 g) were homogenized in 500 ml of 5 mM phosphate buffer (pH 6.0). Insoluble materials and lipid were removed after centrifugation at 10,000× g for 1 hour. Supernatant was applied to a CM-Sepharose Fast Flow (Pharmacia, Piscataway, N.J.) column equilibrated with 5 mM phosphate buffer. After washing, bound proteins were eluted with a NaCl gradient (0–0.3M). The peak containing activity of ribosome inactivation was pooled and dialyzed against PBS using a membrane with molecular weight cut-off of 10,000 daltons.

Antibody and toxin conjugation: MoAb (10 mg) was reacted with a heterobifunctional crosslinking reagent, N-succinimidyl-3-(2-pyridyldithio) propionate (Pharmacia) at 1:3 molar ratio as described by Carlsson et al. (J. Carlsson, et al., *Biochem J.*, 173:723–737 (1978)). Pokeweed antiviral protein (6 mg) was reacted with 2-iminothiolane at 1:3 molar ratio as described previously (J.M. Lambert, et al., *Biochemistry,* 17: 5406–5416 (1978)). Excess of chemicals were removed by gel filtration using a 10PD columm (Bio-Rad, Richmond, Calif.). Chemically modified antibody and PAP-S were combined and incubated at room temperature for 2 hours or at 4° C. overnight. Uncoupled PAP-S was removed by gel filtration on a Sephacryl S-200 (HR) column equilibrated with PBS. The fractions containing antibody and conjugate were pooled, concentrated to 10 ml and then dialyzed against 5 mM phosphate buffer, pH 6.0. Two ml samples containing immunoconjugate and uncoupled antibody were injected into a cation exchange column (Mono S, Pharmacia) equilibrated with 5 mM sodium phosphate buffer, pH 6.0. Immunoconjugate was eluted with a NaCl gradient and absorbance at 280 nm was recorded. The immunoconjugate was eluted as a single peak at 110 mM NaCl. The composition of the immunoconjugate was analyzed by a 7.5% sodium dodecyl sulfate polyacrylamide gel electrophoresis (SDS-PAGE) under a non-reducing condition (Fast System, Pharmacia) along with molecular weight markers (Bio-Rad).

Cytoxicity assay of immunoconjugates: The ability of the immunoconjugate to kill HIV-infected cells was assayed by the inhibition of ($^3$H)-thymidine incorporation of infected cells. H9 cells either uninfected or chronically infected by HIV-1 strains (HTLV-IIIB, HTLV-IIIRF, and HTLV-IIIMN) were maintained in log phase in RPMI1640 supplemented with 15% heat-inactivated fetal bovine serum, 100 U/ml of penicillin and 100 ug/ml of streptomycin. One hundred and eighty ul of 5×10$^4$ cells/ml were dispensed into each well of a 96-well microtiter plate. Twenty ul of purified immunoconjugate of 5-fold serial dilutions (100 ug/ml–160 ng/ml) were added into the wells in triplicates. In some assays in which the specificity of killing by the immunoconjugates was examined, infected H9 cells were incubated with MoAb at 37° C. for 30 minutes prior to addition of the corresponding immunoconjugates. The controls were an irrelevant immunoconjugate of PAP-S or a mixture of the unconjugated antibody and PAP-S at equivalent concentrations under the identical conditions. The cell cultures were kept at 37° for 24 hours and pulsed with 1 uCi per well of ($^3$H)-thymidine for another 4 hours. Cells were harvested on glass fiber filters using a Skatron cell harvester and the ($^3$H)-thymidine retained on the dry filter was measured by scintillation counting. The inhibition of cellular thymidine incorporation was calculated by comparing the radioactivity of test cultures to that of the control.

Flow cytometry: The binding activity of the immunoconjugates to H9 cells infected by HTLV-IIIB was studied by flow cytometry. Briefly, H9 cells in the log phase uninfected or infected by HIV-1 were washed twice in PBS containing 1% bovine serum albumin at 4° C. The cells were resuspended at 1×10$^7$/ml in the same buffer. Fifty ul of the cell suspension were incubated with 50 ul of diluted immunoconjugates (10–0.1 ug/ml) at 4° C. for 30 minutes. The cells were then washed with 3 ml of the buffer. Then 50 ul of goat anti-mouse F(ab')$_2$ conjugated with fluorescein isothiocyanate (1:10 dilution) was added, and the mixture was incubated for another 30 minutes at 4° C. The cells were then washed with 3 ml of the buffer and fixed with 0.5 ml 1% paraformaldehyde and assayed by flow cytometry.

Results

Figure 3:
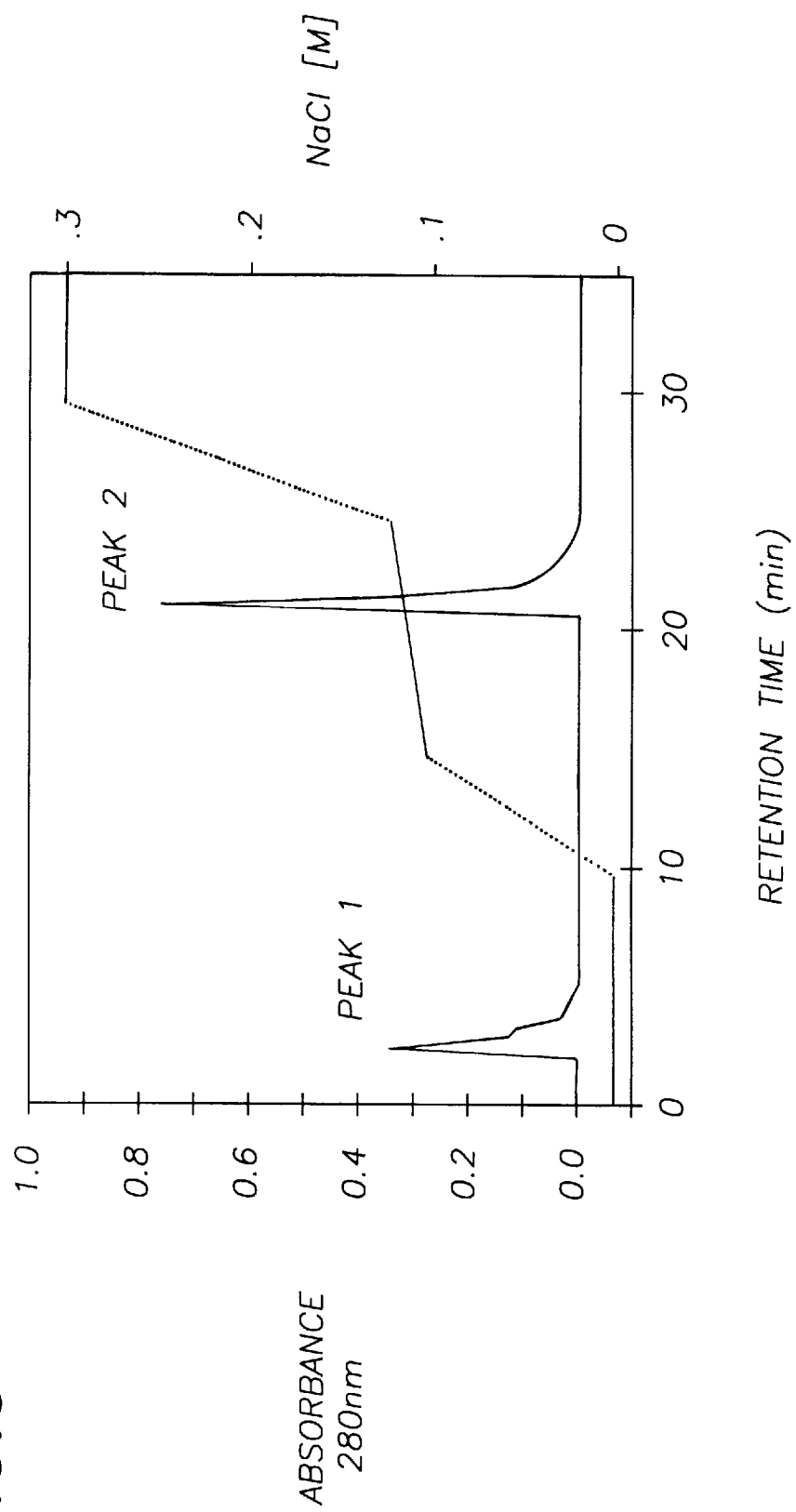
Figure 4:
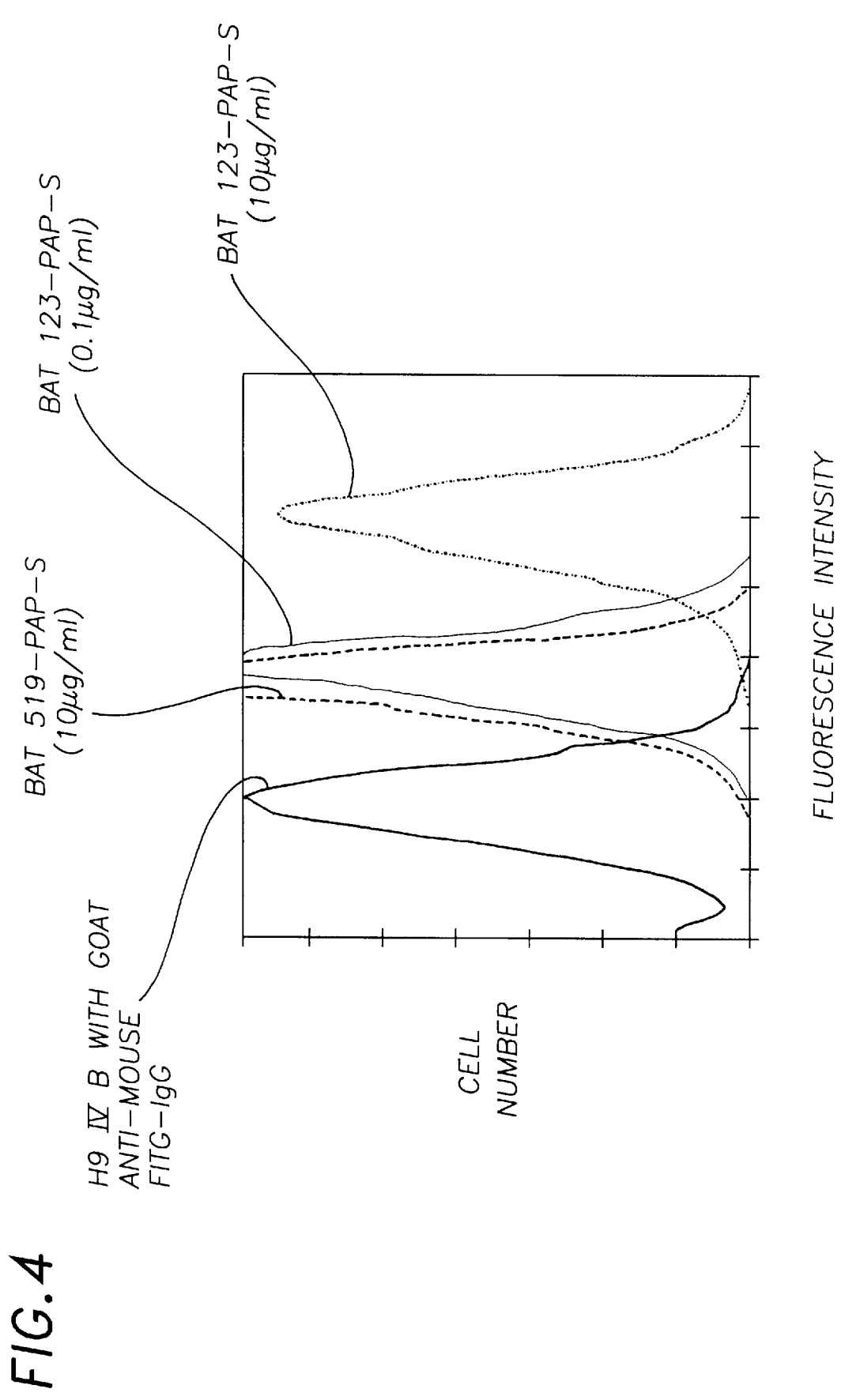

Purification and characterization of immunoconjugates: Immunoconjugate was isolated from uncoupled MoAb using a cation exchange column (Mono S). Since the isoelectric points of both MoAb BAT123 and G3.519 are approximately 6.8, unmodified MoAb did not bind to the column during the sample loading in 5 mM phosphate buffer, pH 6.0. The immunoconjugate was eluted from the Mono S column as a single peak at 110 mM NaCl concentration (FIG. 3). However, this peak, when analyzed by 7.5% SDS-PAGE under the non-reducing condition, resolved into two protein bands. The higher molecular weight band represented the conjugate containing two molecules of PAP-S per molecule of antibody and the lower band a conjugate with one molecule of PAP-S per antibody molecule. Densitometric analysis of Coomassie blue stained gels indicated that the higher molecular weight conjugate accounted for about 25% of the total immunoconjugates (data not shown). The binding activity of the immunoconjugates determined by ELISA using synthetic oligopeptides comprising the binding epitopes of the respective MoAbs revealed no impairment of antibody activity after conjugation (data not shown). Both MoAb BAT123 and G3.519 are specific to gp120 but recognize distinct epitopes with different binding constants (2.9×10$^{10}$ M$^{-1}$ and 6.9×10$^8$ M$^{-1}$ respectively). As shown in FIG. 4, BAT123-PAP-S bound more than 90% of HTLV-IIIB-infected H9 cells at 0.05 ug/ml, while G3.519-PAP-S required 5 ug/ml to show the same degree of binding.

Figure 5:
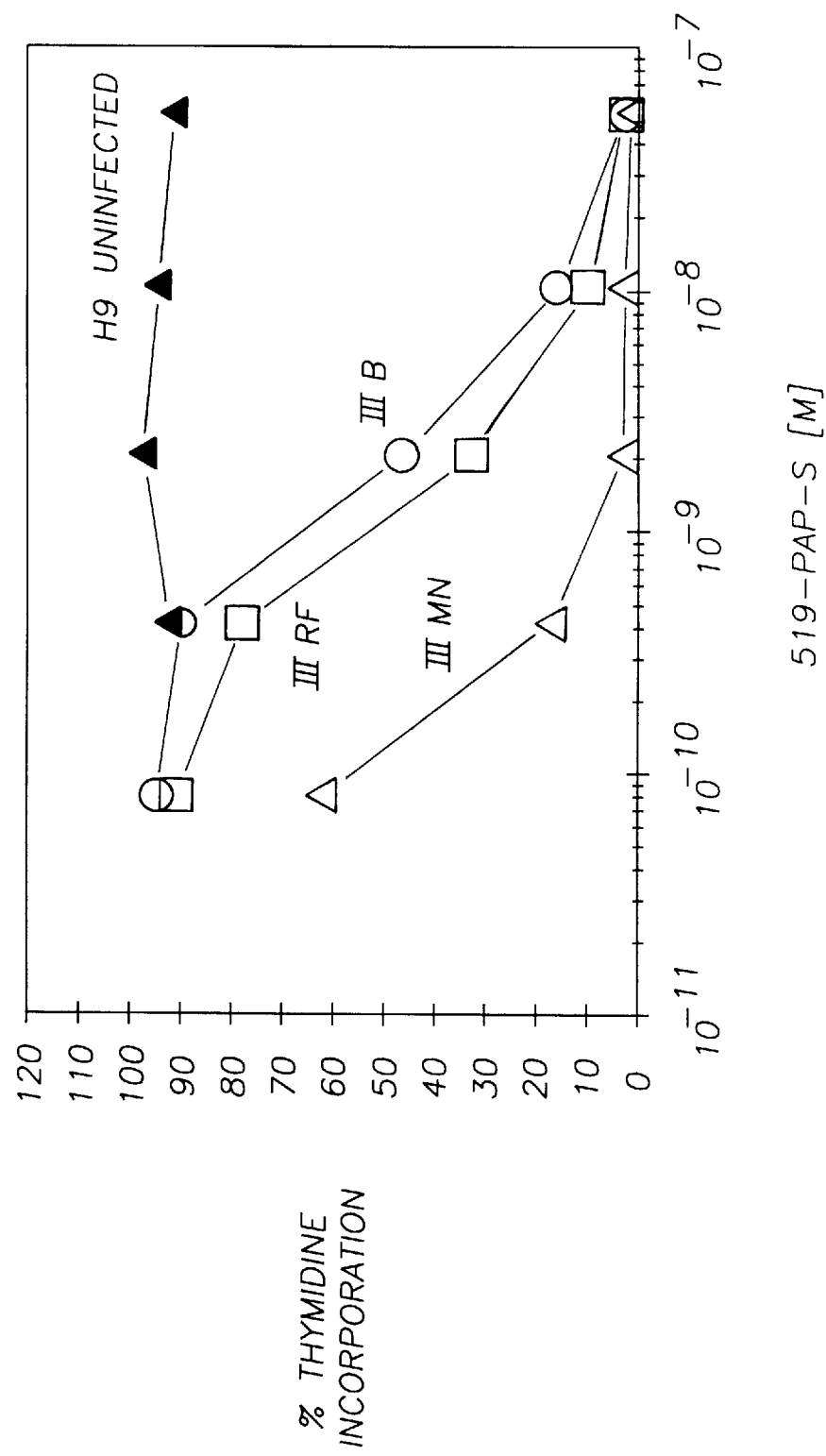

Cytotoxicity of G3.519-PAP-S on HIV-1 infected cells: G3.510-PAP-S binds to the CD4-binding region of gp120 in which the amino acid sequence is conserved. H9 cells infected separately with three diverse strains of HIV-1 were all sensitive to G3.519-PAP-S treatment (FIG. 5). The immunoconjugate killed H9 cells infected with HTLV-IIIMN more effectively (IC$_{50}$=1.4×10$^{-10}$ M) than it killed H9 cells infected with HTLV-IIIB (IC$_{50}$ =1.7 ×10$^{-9}$ M) and HTLV-IIIRF (IC$_{50}$ =1.2×10$^{-9}$ M). In contrast to the differing cytotoxic activity exhibited by BAT123-PAP-S against H9 cells infected with HTLV-IIIB and HTLV-IIIRF, H9 cells infected with those strains were equally sensitive to G3.519-PAP-S (FIG. 3). G3.519-PAP-S was not cytotoxic to uninfected H9 cells up to a concentration of 5.3×10–8 M.

Figure 6:
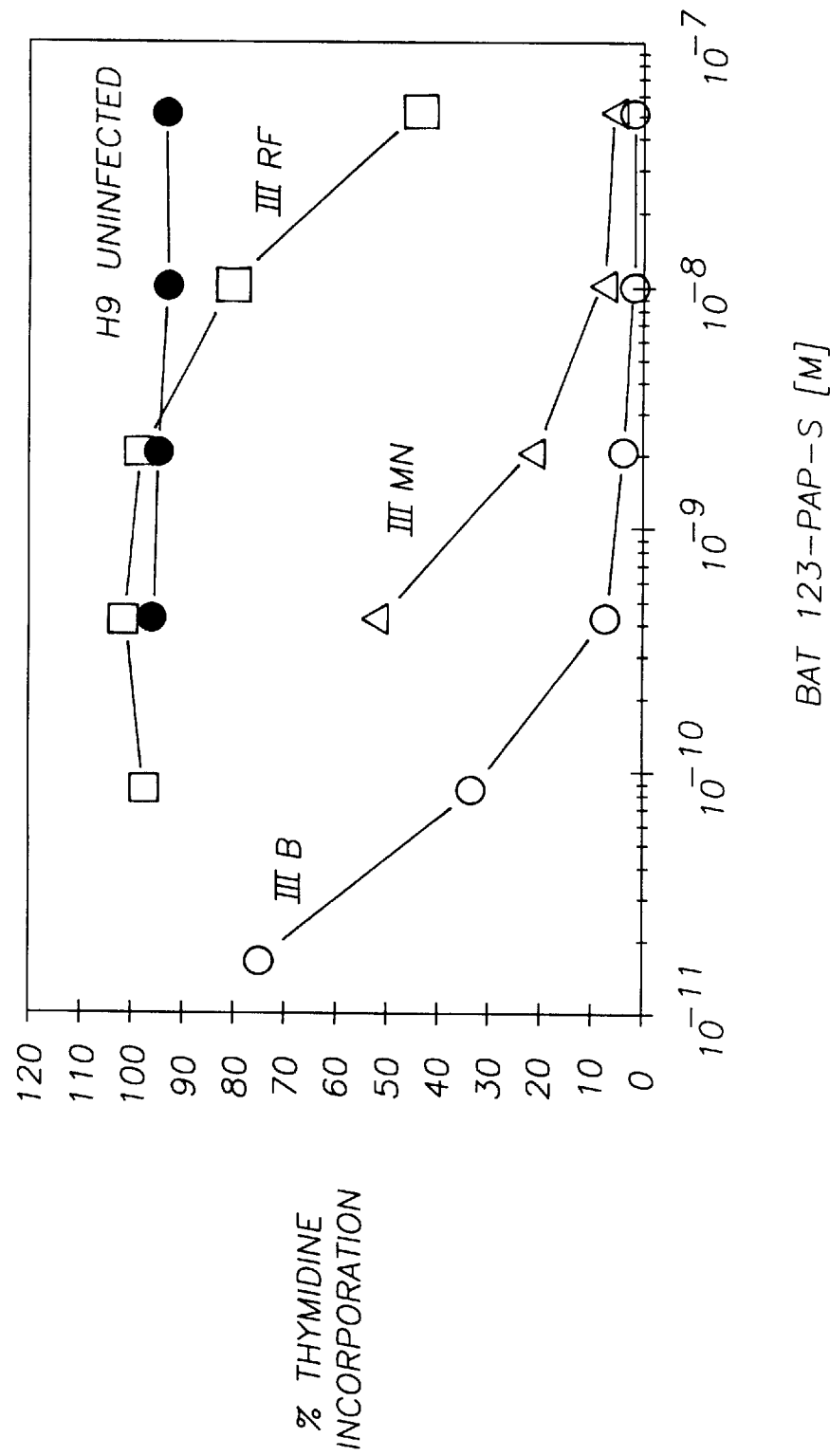

Cytotoxicity of BAT123-PAP-S on HIV-1-infected cells: The cytotoxic activity of the BAT123-PAP-S immunoconjugate was evaluated using H9 cells infected with the same diverse strains or HIV tested with G3.519-PAP-S. Incubation of H9 cells infected by these diverse strains of HIV-1 with BAT123-PAP-S showed various degrees of specific killing (FIG. 6). H9 cells infected with HTLV-IIIB were most susceptible to BAT123-PAP-S treatment with an IC$_{50}$ of 5.2×10$^{-11}$ M. At 2.6×10$^{-9}$ M BAT123-PAP-S inhibited DNA synthesis by more than 90%. BAT123-PAP-S also killed H9 cells infected with HTLV-IIIMN (IC$_{50}$ =4.9×10$^{-9}$ M). However, BAT123-PAP-S was relatively ineffective in killing H9 cells infected with the HTLV-IIIRF strain (IC$_{50}$ =3.9×10$^{-8}$ M). BAT123-PAP-S did not inhibit DNA synthesis of uninfected H9 cells up to a concentration of 5.3×10$^{-8}$ M.

Specific cytotoxicity of immunoconjugates: The specificity of immunoconjugates against target cells was studied by antibody blocking experiments. As shown in FIG. 7, addition of specific MoAb prior to the incubation of target cells with the immunoconjugates efficiently blocked the cytotoxicity of immunoconjugates in a dose-dependent fashion. BAT123-PAP-S at 60 ng/ml inhibited 90% of DNA synthesis of H9 cells infected with HTLV-IIIB strain. Addition of 4 ug/ml of BAT123 abolished approximately 60% of its cytotoxicity. Similarly, G3.519-PAP-S at 0.6 ug/ml inhibited 55% of DNA synthesis of H9 cells infected with HTLV-IIIB. In the presence of 50 fold excess of MoAb G3.519, the immunoconjugate inhibited only 13% of DNA synthesis of target cells. Irrelevant monoclonal antibody did not inhibit the cytotoxicity of immunoconjugates even at 200 fold excess of the free antibody. In addition, irrelevant MoAb containing PAP-S did not show any cytotoxicity against H9 cells infected with HTLV-IIIB (data not shown).

Discussion

Two immunoconjugates were synthesized by chemically coupling different murine neutralizing monoclonal antibodies which recognize gp120 of HIV-1 to PAP-S through a disulfide bond linkage. These immunoconjugates, designated BAT123-PAP-S and G3.519-PAP-S, showed specific cytotoxicity against human T cells infected with HIV-1. Epitope mapping studies using synthetic polypeptides revealed that MOAB BAT123 recongizes the relatively variable region (amino acid 304–318) of gp120 and MoAb G3.519 recognizes a relatively conserved region (amino acid 423–433) of gp120.

When tested against H9 cells infected with HTLV-IIIB, BAT123-PAP-S showed cytotoxic effectiveness at lower concentrations than G3.519-PAP-S (IC $_{50}$ $5.2\times10^{-11}$ M vs $1.7\times10^{-9}$M). The increased effectiveness of BAT123-PAP-S with HTLV-IIIB infected H9 cells may result from the higher affinity of BAT123 antibody and/or the location of the epitope on gp120, since both immunoconjugates contained PAP-S and the same target cells were used in the studies.

Although BAT123 is directed against the variable region in gp120 of HTLV-IIIB, BAT123-PAP-S still was effective in killing H9 infected with HTLV-IIIMN while H9 cells infected with HTLV-IIIRF were not effectively killed. However, in neutralization studies, BAT123 showed a similar degree of ineffectiveness against both HTLV-IIIRF and HTLV-IIIMN. The recent data with BAT123-PAP-S showing its ability to kill H9 cells infected with both HTLV-IIIB and HTLV-IIIMN suggests a broader application of this antibody for use as an immunoconjugate.

Epitope mapping of G3.519 revealed that the binding site of the antibody resides on the CD4 binding region of gp120 which is conserved among diverse strains of HIV. G3.519-PAP-S specifically killed H9 cells infected with three diverse strains. It is interesting to note that even though MoAb G3.519 was generated against gp120 of the HTLV-IIIB strain, H9 cells infected with HTLV-IIIMN strain were more sensitive to G3.519-PAP-S than H9 cells infected with HTLV-IIIB (FIG. 5, $IC_{50}=1.4\times10^{-10}$ M for HTLV-IIIMN vs. $1.7\times10^{-9}$ M for HTLV-IIIB).

These in vitro studies clearly show that immunoconjugates directed to the CD4 binding region of gp120 are effective in killing human T cells infected with diverse strains of HIV-1. These immunoconjugates may have a longer half-life in vivo as compared to the sCD4-toxin conjugates (which are known to be cleared rapidly in vivo (D.J. Capon, et al., *Nature,* 337: 525–531 (1989)), and may represent a better approach for specific killing of HIV infected cells.

The cell lines producing BAT123 and BAT267 were respectively deposited on Apr. 20, 1990 and Dec. 14, 1990 at the American Type Culture Collection, 12301 Parklawn Drive, Rockville, Md.

Equivalents

It should be understood that the terms, expressions, and descriptions herein are for clarification only and not limitation, and that the scope of protection is limited only by the claims which follows.

We claim:

1. An antibody conjugate comprising a monoclonal antibody which binds to an epitope within amino acid residue numbers 308–322 of gp120 and which neutralizes HIV-1, conjugated with a cytotoxic agent, an anti-viral agent or an agent which facilitates passage through the blood-brain barrier.

2. An antibody conjugate of claim 1 wherein the antibody is BAT123.

3. An antibody conjugate of claim 1 wherein the cytotoxic or anti-viral agent is selected from the group consisting of pokeweed antiviral proteins, gelonin, abrin, ricin, cytotoxic steroids, phospholipases, interferons, radioactive nuclides, azidothymidine, and ribovirin.

4. An antibody conjugate comprising a monoclonal antibody which binds to an epitope within amino acid residue numbers 298–312 of gp120 and which neutralizes HIV-1, conjugated with a cytotoxic agent, an anti-viral agent or an agent which facilitates passage through the blood-brain barrier.

* * * * *